United States Patent [19]
L'Italien et al.

[11] Patent Number: 6,136,784
[45] Date of Patent: Oct. 24, 2000

[54] AMYLIN AGONIST PHARMACEUTICAL COMPOSITIONS CONTAINING INSULIN

[75] Inventors: James L'Italien, Del Mar, Calif.; Shankar Musunuri, Exton, Pa.; Kale Ruby, San Diego; Orville Kolterman, Poway, both of Calif.

[73] Assignee: Amylin Pharmaceuticals, Inc., San Diego, Calif.

[21] Appl. No.: 09/005,240

[22] Filed: Jan. 9, 1998

Related U.S. Application Data

[60] Provisional application No. 60/035,141, Jan. 8, 1997.
[51] Int. Cl.[7] ............................. A61K 38/00; A61K 38/28
[52] U.S. Cl. ..................................... 514/12; 514/3; 514/4; 514/21; 514/866
[58] Field of Search ........................ 514/12, 3, 4

[56] References Cited

U.S. PATENT DOCUMENTS 5,175,145  12/1992  Cooper .......................................... 514/4
5,686,411  11/1997  Gaeta et al. ................................. 514/12

*Primary Examiner*—F. T. Moezie
*Attorney, Agent, or Firm*—Lyon & Lyon LLP

[57] ABSTRACT

The present invention is concerned with a pharmaceutical formulation in a container, for example, a vial, prefilled cartridge, prefilled syringe or disposable pen, comprising approximately 0.01 to about 0.5% (w/v) amylin agonist, preferably pramlintide, in an aqueous system along with approximately 0.02 to about 0.5% (w/v) of an acetate, phosphate, citrate, or glutamate buffer to a pH of the final composition of approximately 3.0 to about 6.0 as well as approximately 1.0 to 10% (w/v) of a carbohydrate or polyhydric alcohol tonicifier; and, optionally, approximately 0.005 to 1.0% (w/v) of a preservative selected from the group consisting of m-cresol, benzyl alcohol, parabens and phenol. These formulations maintain stability upon storage under refrigerated or room temperature conditions. Such formulations can be further combined with insulin in the same syringe for administration to a patient.

8 Claims, 14 Drawing Sheets

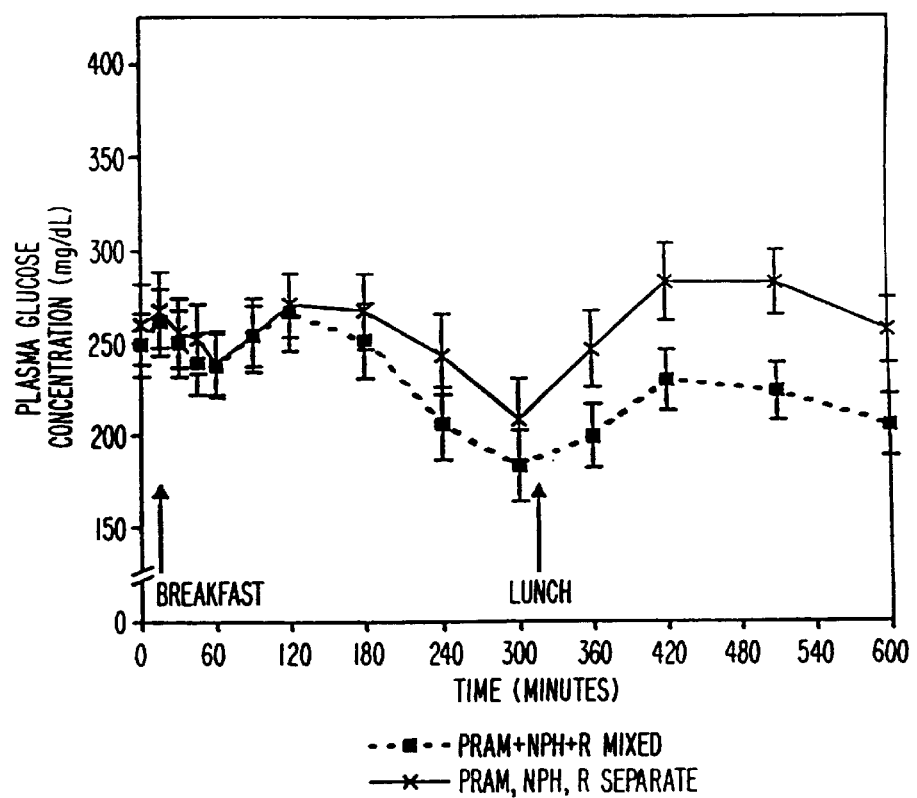
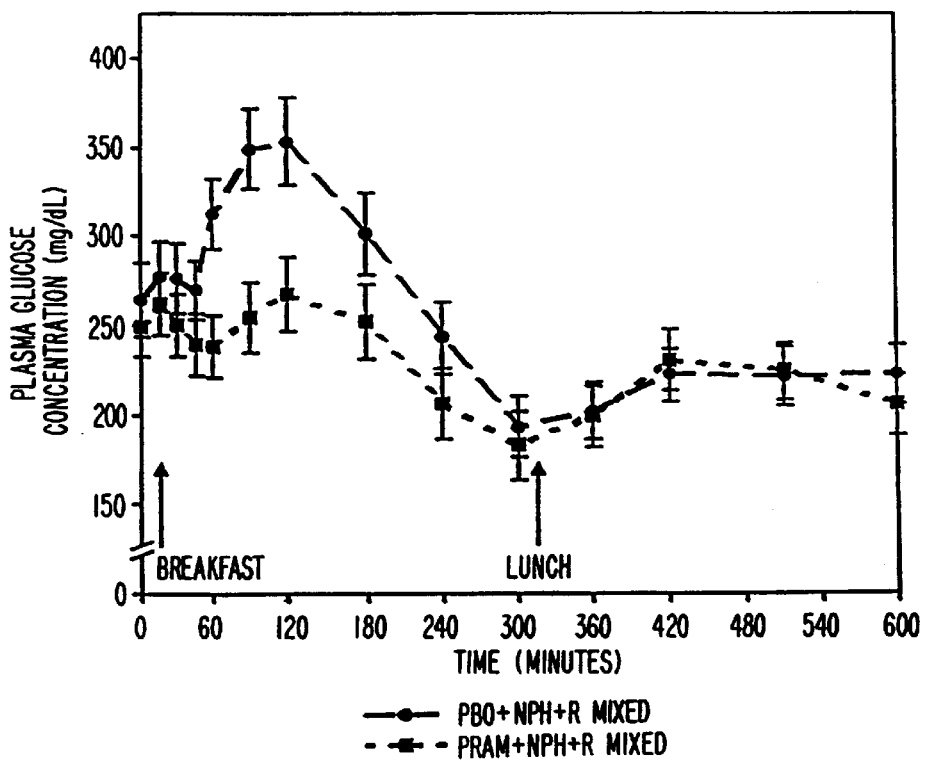

AMYLIN AGONIST PHARMACEUTICAL COMPOSITIONS CONTAINING INSULIN

This application claims the benefit of U.S. Pat. No. 60/035,141, filed Jan. 8, 1997, now abandoned, the contents of which are hereby incorporated in their entirety.

FIELD OF THE INVENTION

The present invention relates to pharmaceutical compositions containing an agonist of amylin and an intermediate-acting insulin. More particularly, the invention relates to pharmaceutical compositions containing one or more amylin agonists or amylins and one or more intermediate-acting insulins, such as NPH insulin. The invention also relates to the preparation and use of such pharmaceutical compositions in the treatment of a mammal, preferable a human, who use insulin to control their blood glucose concentration, particularly people with diabetes, either alone or in combination with another insulin or glucose-lowering agent.

BACKGROUND

Diabetes

Diabetes mellitus is a major global health problem which is inadequately treated by available drugs. The International Diabetes Federation has estimated that over 100 million people worldwide are afflicted with this disease. Diabetes costs the American economy over $100 billion annually, according to a study reported in the *Journal of Clinical Endocrinology and Metabolism*, which went on to say that ". . . health care expenditures for people with diabetes constituted about one in seven health care dollars spent in 1992. " Moreover, the American Medical Association reports that the incidence of diagnosed diabetes as a percentage of the American population has tripled since 1958, and that the total number of diagnosed and undiagnosed cases has grown to about 16 million.

Diabetes is the name given to the clinical description of patients with a number of symptoms arising from raised blood glucose levels. The metabolism of glucose involves many organs, in each of which several important metabolic steps occur. Key regulatory points include hepatic regulation of glucose uptake and release, muscle utilization of fuels, control by pancreatic production of insulin and glucagon, and neurogenic controls. Diabetes may arise from abnormalities at one or several sites in the complex feedback loops in this system.

Two main types of diabetes can be distinguished: (1) insulin-dependent diabetes mellitus (previously termed "juvenile-onset," and now called "IDDM" or "Type 1"), and (2) non-insulin-dependent diabetes mellitus (previously ermed "maturity-onset," and now called "NIDDM" or "Type 2"). Other forms of diabetes include (3) maturity-onset or non-insulin-dependent diabetes in the young (a rare dominantly inherited, mild type of disease); (4) diabetes mellitus or carbohydrate intolerance associated with certain genetic syndromes; (5) secondary diabetes mellitus (e.g., drug-induced, from pancreatic disease, hormonal or receptor abnormalities, etc.), and (6) gestational diabetes mellitus. Different nomenclatures for these types have arisen because overlap between the types has made a strict, simple classification covering all patients difficult.

Typically, diabetes occurs when the pancreas no longer produces enough insulin, a hormone that regulates the metabolism of blood glucose. In Type 1 diabetes, which afflicts about 10% of all people with diagnosed diabetes in developed countries, the pancreatic beta cells that make insulin have been destroyed. In the more prevalent form of diabetes, Type 2 diabetes, the insulin-producing cells are unable to produce enough insulin to compensate for the patient's poor sensitivity to the hormone in glucose-using tissues such as skeletal muscle (a condition called insulin resistance). In both Type 1 and Type 2 diabetes, the insulin deficiency results in an abnormally high blood-glucose concentration (a condition called hyperglycemia) hich is an important cause of the degenerative complications associated with diabetes, including blindness, kidney failure and nerve damage. In addition, many authorities believe hyperglycemia plays a role in the development of heart disease.

One of the main features of Type 1 diabetes is the sudden appearance in non-obese children or young adults of a severe disease which only responds satisfactorily to insulin therapy. On the other hand, Type 2 patients tend to present at an older age, are often obese and then respond to diet, without need for insulin therapy. The "juvenile" diabetes and "maturity" diabetes nomenclature based on the age of onset has fallen out of fashion with the realization that auto-immunity to the islets is the characteristic pathology of Type 1 diabetes, and that this is not confined to juvenile-onset but can occur in maturity-onset diabetes and may present at any age. However, the distinction based on age is still sometimes used as a shorthand description of presentation.

The advent of insulin therapy led to the clinical classification of the two main types of diabetes as "insulin-dependent" and "non-insulin-dependent," which relate to the empirical requirement for insulin therapy. This was introduced because some maturity-onset diabetic patients are of normal weight, have severe disease which requires insulin, and resemble juvenile-onset diabetic patients. Although IDDM is defined by the patient's dependence on insulin for survival, in practice this definition is often extended to include patients who require insulin therapy to prevent symptoms. Similarly, the term NIDDM is often restricted to patients who can be maintained symptom-free either by diet or by tablet therapy. This usage is not strictly correct because, as noted below, patients who present with NIDDM may later develop more severe diabetes that requires insulin therapy. In practice, a Type 2 patient initially treated by diet or tablets, but later transferred to insulin, is often termed an insulin-treated NIDDM patient.

Insulin

Since its discovery in 1921, insulin replacement therapy has played a central role in treating diabetes. For people with Type 1 diabetes, insulin injections are essential, since these patients would otherwise die. For people with Type 2 diabetes, oral medications that either stimulate greater insulin production or enhance insulin sensitivity may improve metabolic control. However, as many as 20% of people with newly diagnosed Type 2 diabetes do not respond to oral therapy. Moreover, patients who do respond to oral therapy become progressively resistant over time, with as many as 10% each year ceasing to derive a therapeutic benefit. Thus, an estimated 40% of people diagnosed with Type 2 diabetes are using insulin injections to manage their disease. It has been estimated that in North America, Europe and Japan alone, as many as two million people with Type 1 diabetes and five million people with Type 2 diabetes use insulin to help control their blood-glucose concentrations.

Because insulin given by mouth is digested as a dietary protein, it has to be administered by injection. Various advances and changes have been made in the United States and Europe in the purity and formulation of insulin preparations. These have resulted in the marketing of mono-species insulins (porcine, bovine, and human) of very high purity. Human insulin is most commonly synthesized in either *E. coli* or yeast cells that have been genetically altered by recombinant DNA technology, but may also be prepared by a semi-synthetic process from porcine insulin.

Prior to 1973, insulin preparations available for therapeutic use contained, as potentially antigenic components, significant amounts of proinsulin and its incompletely converted products as well as other pancreatic hormones. New procedures were devised to prepare purer preparations of the hormone. Two such preparations are "single-peak" insulin and "single-component" insulin; the latter is designated as "purified." The purity of commercial insulin in the United States is now at least that of "single-component" insulin (99%). These "purified" insulins contain not more than 10 parts per million of proinsulin. "Purified" porcine insulin is the least immunogenic of the nonhuman insulins available.

All regular insulin preparations in the United States are now supplied at neutral pH. This has resulted in improved stability of the hormone, and patients need no longer refrigerate the vial of insulin in use. Furthermore, neutral regular insulin can be mixed in any desired proportion with other, modified insulin preparations since all marketed insulin preparations will be at a similar pH. Preparations of insulin have been divided into three general categories according to promptness, duration, and intensity of action following subcutaneous administration. They are classified as fast-, intermediate-, and long-acting insulins. There are also various types of insulins within these categories. They include regular insulins, protamine zinc insulins, NPH insulins, semilente insulins (prompt insulin zinc suspensions), lente insulins (insulin zinc suspensions), and ultralente insulins (extended insulin zinc suspensions).

Crystalline insulin is prepared by the precipitation of the hormone in the presence of zinc (as zinc chloride) in a suitable buffer medium. Crystalline insulin when dissolved in water is also known as regular insulin. Following subcutaneous injection, it is rapidly absorbed (15–60 minutes). Its action is prompt in onset and relatively short in duration, i.e., it reaches its peak effect in about 1.5 to 4 hours, and lasts for about 5–9 hours.

By permitting insulin and zinc to react with the basic protein protamine, Hagedorn and associates prepared a protein complex, protamine zinc insulin. When this complex is injected subcutaneously in an aqueous suspension, it dissolves only slowly at the site of deposition, and the insulin is absorbed at a retarded but steady rate. Protamine zinc suspension insulin has largely been replaced by isophane insulin suspension, also known as NPH insulin; the N denotes a neutral solution (pH 7.2), the P refers to the protamine zinc insulin content, and the H signifies the origin in Hagedorn's laboratory. It is a modified protamine zinc insulin suspension that is crystalline. The concentrations of insulin, protamine, and zinc are so arranged that the preparation has an onset and a duration of action intermediate between those of regular insulin and protamine zinc insulin suspension. Its effects on blood sugar are indistinguishable from those of an extemporaneous mixture of 2 to 3 units of regular insulin and 1 unit of protamine zinc insulin suspension.

Chemical studies have revealed that the solubility of insulin is determined in important measure by its physical state (amorphous, crystalline, size of the crystals) and by the zinc content and the nature of the buffer in which it is suspended. Insulin can thus be prepared in a slowly absorbed, slow-acting form without the use of other proteins, such as protamine, to bind it. Large crystals of insulin with high zinc content, when collected and resuspended in a solution of sodium acetate-sodium chloride (pH 7.2 to 7.5), are slowly absorbed after subcutaneous injection and exert an action of long duration. This crystal preparation is named extended insulin zinc suspension (ultralente insulin). Amorphous insulin precipitated at high pH is almost as rapid in onset than regular insulin, but has a somewhat longer duration of action. This amorphous preparation is named prompt insulin zinc suspension (semilente insulin). These two forms of insulin may be mixed to yield a stable mixture of crystalline (7 parts) and amorphous (3 parts) insulin—called insulin zinc suspension (lente insulin)—that is intermediate in onset and duration of action between semilente and ultralente preparations and is similar to NPH insulin.

In summary, the fast-acting insulins include the regular insulins and the prompt insulin zinc suspensions (semilente insulins). The intermediate-acting insulins include the isophane insulin suspensions (NPH insulins, isophane insulin) and the insulin zinc suspensions (lente insulins). The long-acting insulins include protamine zinc insulin suspensions, and extended insulin zinc suspensions (ultralente insulins). Most of these preparations are available as either porcine or bovine insulins. Human insulins of recombinant DNA origin are available as regular and isophane insulins and as insulin zinc suspensions. Recently, a modified insulin (Lys(B28), Pro(B29) human insulin analog, created by reversing the amino acids at positions 28 and 29 on the insulin B-chain) has been introduced. It is a fast-acting insulin, with a more rapid onset of glucose lowering action, an earlier peak action, and a shorter duration of action than regular human insulin.

Many insulins are available from a number of companies. These include Eli Lilly & Company and Novo Nordisk, two of the largest suppliers of insulin in the world. Fast-acting insulins available from Eli Lilly include (1) Iletin® I (Regular); (2) Regular Iletin® II (Pork, 100 Units); (3) Regular Iletin® II (Concentrated, Pork, 500 Units); (4) Humalog® Injection (insulin lyspro, recombinant DNA origin); and (5) Humulin® R (regular insulin, recombinant DNA origin, 100 Units). Fast-acting insulins available from Novo Nordisk include (1) Novolin® R (Regular, Human Insulin Injection (recombinant DNA origin) 100 Units); (2) Novolin® R PenFill 1.5 ml Cartridges (Regular, Human Insulin Injection (recombinant DNA origin) 100 Units); (3) Novolin® R Prefilled™ (Regular, Human Insulin Injection (recombinant DNA origin) in a 1.5 ml Prefilled Syringe, 100 units/ml); (4) Regular Purified Pork Insulin (100 Units/ml); and (5) Velosulin® BR (Buffered Regular Human Insulin Injection, 100 Units/ml). Intermediate-acting insulins available from Eli Lilly include (1) Humulin® 50/50 (50% human insulin isophane suspension and 50% human insulin injection (rDNA origin), 100 Units); (2) Humuline® 70/30 (70% human insulin isophane suspension and 30% human insulin injection (rDNA origin), 100 Units); (3) Humulin® L (lente; human insulin (rDNA origin) zinc suspension, 100 Units); ); (4) Humulin® N (NPH; human insulin (rDNA origin) isophane suspension, 100 Units); (5) Lente® Iletin® I, (insulin zinc suspension, beef-pork); (6) NPH Iletin® I (isophane insulin suspension, beef-pork); (7) Lente Iletin® II (insulin zinc suspension, purified pork); and (8) NPH Iletin® II, (isophane insulin suspension, purified pork). Intermediate-acting insulins available from Novo Nordisk include (1) Novolin® L (Lente, Human Insulin Zinc Suspension (recombinant DNA origin), 100 Units/ml); (2) Novolin® N (NPH, Human Insulin Isophane Suspension (recombinant DNA origin), 100 Units/ml); (3) Novolin® N PenFill® 1.5 ml Cartridges; (4) Novolin® N Prefilled™ (NPH, Human Insulin Isophane Suspension (recombinant DNA origin) in a 1.5 ml Prefilled Syringe, 100 Units/ml); (5) Novolin® 70/30 (70% NPH, Human Insulin Isophane Suspension and 30% Regular, Human Insulin Injection (recombinant DNA origin), 100 Units/ml); (6) Novolin® 70/30 PenFill® 1.5 ml Cartridges; (7) Novolin® 70/30 Prefilled™ (70% NPH, Human Insulin Isophane Suspension and 30% Regular, Human Insulin Injection (recombinant DNA origin) in a 1.5 ml Prefilled Syringe, 100 Units/ml); (8) Lente Purified Pork Insulin (Zinc Suspension, USP 100 Units/ml); and (9) NPH Purified Pork Isophane Insulin Suspension (100 Units/ml). Long acting insulins include Eli Lilly's Humulin® U (Ultralente® human insulin (recombinant DNA origin) extended zinc suspension).

Normal people produce half their insulin at a low, basal rate and half in response to meals. The insulin response to meals occurs within 5 minutes and lasts for 2–3 hours following each meal. Despite 75 years of efforts to improve insulin therapy, most people with diabetes have great difficulty achieving optimal glucose control with insulin alone. For superior glucose control, each insulin injection should be adjusted to reflect the person's pre-meal blood-glucose concentration, the carbohydrate content of the meal, and the individual's planned level of physical activity. The basal insulin supply can be given to diabetic patients using a long-acting, crystalline insulin which is slowly absorbed. The major difficulty comes in coping with meals, since soluble insulin takes 30 minutes to be absorbed from a subcutaneous injection (i.e., it should be given 30 minutes before a meal) and lasts for 4–6 hours. This long time-course is inconvenient and a snack often has to be taken 2–3 hours after injection to cover the prolonged insulin absorption. In addition, absorption of insulin varies from injection to injection. The insulin requirements of a patient are also less after exercise and greater when stressed or ill. Therefore, most patients continue to have high glucose levels, and aggressive efforts to bring blood-glucose concentration down into the normal range (a condition called normoglycemia) using intensive insulin therapy increase the risk of blood-glucose concentration falling too low (a condition called hypoglycemia), which can cause unpleasant and dangerous effects including sweating, disorientation, personality changes, coma, convulsions and even death. If normoglycemia is to be achieved, patients need to be attentive to their life-style and assess the response to their insulin therapy by measuring their blood glucose. This is done by pricking a finger and placing the blood onto a strip containing the enzyme glucose oxidase; the glucose concentration is determined either by an electronic sensor or by a color change monitored visually. Many patients do this regularly four times per day, before meals and before bed, in order to assess the appropriate insulin doses, although others find this unacceptable. Indeed, to avoid hypoglycemia, many people with diabetes maintain high blood-glucose concentrations and thereby increase their risk of degenerative complications from the disease.

Diet therapy, inducing weight reduction, may be sufficient to reduce the blood glucose to below the renal threshold and to make people with Type 2 diabetes symptom-free, although it is rarely sufficient to induce normal fasting glucose levels. If symptoms persist despite dietary therapies, then most physicians treat with tablets containing sulphonylureas to stimulate insulin secretion. This approximately doubles the β-cell efficiency, but, nevertheless, continued symptom-free hyperglycemia with a fasting glucose level of 9–10 mmol/l is common. "Second generation" drugs such as glibenclamide or glipizide are no more effective than "first generation" drugs such as tolbutamide or chlorpropamide.

Biguanide therapy with metformin, to improve glucose uptake is an alternative, but like a sulphonylurea it only induces a modest decrease of blood glucose. If symptoms recur on diet and tablet therapy, patients are transferred to insulin therapy.

Although most people with diabetes cannot maintain their blood glucose concentrations near the normal range with insulin alone, it is now established that even modest improvements in glucose control can result in significant reductions in the risk of degenerative complications such as blindness, kidney failure and nerve damage. In other words, the maintenance of a normal blood glucose concentration has been shown to prevent diabetic complications and maintain health.

In June 1993, the National Institutes of Health announced the results of the Diabetes Control and Complications Trial ("DCCT"). This decade-long, prospective study of over 1,400 people with Type 1 diabetes established the importance of glucose control as a determinant of long-term risk of degenerative complications. The quality of glucose control for each DCCT participant was determined by measuring the proportion of blood-hemoglobin which had chemically combined with blood-glucose to form glycated hemoglobin (HbA1c). This measurement is a recognized indicator of average blood-glucose concentration over the three- to four-month period prior to testing, and lower glycated hemoglobin values are indicative of better glucose control. In this regard, the data from the DCCT showed definitively that the risk of degenerative complications is greatly reduced if blood-glucose concentrations in people with Type 1 diabetes can be brought closer to the concentrations measured in non-diabetic individuals. However, the intensive insulin therapy used to achieve this benefit had several side effects and disadvantages, including (1) a three-fold increase in severe hypoglycemia (defined as low blood sugar episodes which rendered the individual incapable of treating themselves such that the intervention of another person was required compared) with the control group, (2) an average weight gain of 10 to 15 pounds per patient, (3) a highly burdensome treatment regimen requiring strict patient compliance, and (4) intensive and costly support from diabetes care-givers. As a result of these side effects and disadvantages, most people using insulin currently are unable to achieve normal blood-glucose concentrations.

Thus, advances in insulin preparations have not led to the elimination of hyperglycemia, which in turn leads to the degenerative complications of diabetes. It is understood that, in order to achieve normoglycemia in most patients, new technology will need to be developed. In view of the health problems and economic costs associated with this failure to achieve optimal glucose control a new drug which could safely help people with diabetes improve their glucose control without imposing unacceptable treatment burdens would be of great therapeutic benefit.

Amylin

In 1987, researchers at the University of Oxford reported that the pancreatic beta-cells which make insulin also produce a second peptide, amylin. Amylin is a 37 amino acid protein hormone that is co-secreted with insulin from the beta cells of the pancreas in response to a meal. This hormone in healthy individuals is believed to work in concert with insulin in controlling glucose metabolism. The structure and biology of amylin have previously been reviewed. See, for example, Rink et al., Trends in *Pharmaceutical Sciences*, 14:113–118 (1993); Gaeta and Rink, *Med. Chem. Res.*, 3:483–490 (1994); and, Pittner et al., *J. Cell. Biochem.*, 55S:19–28 (1994). Amylin is the subject of U.S. Pat. No. 5,367,052, issued Nov. 22, 1995.

Excess amylin action has been said to mimic key features of Type 2 diabetes and amylin blockade has been proposed as a novel therapeutic strategy. It has been disclosed in U.S. Pat. No. 5,266,561, issued Nov. 30, 1993, that amylin causes reduction in both basal and insulin-stimulated incorporation of labeled glucose into glycogen in skeletal muscle. The latter effect was also disclosed to be shared by calcitonin gene related peptide (CGRP) (see also Leighton and Cooper, *Nature*, 335:632–635 (1988)). Amylin and CGRP were approximately equipotent, showing marked activity at 1 to 10 nM. Amylin is also reported to reduce insulin-stimulated uptake of glucose into skeletal muscle and reduce glycogen content (Young et al., *Amer. J. Physiol.*, 259:45746–1 (1990)). The treatment of Type 2 diabetes and insulin resistance with amylin antagonists is disclosed.

In Type 1 diabetes, amylin has been shown to be missing or deficient and combined replacement with insulin has been proposed as a preferred treatment over insulin alone in all forms of diabetes. It has been proposed that the lack of amylin contributes to poor glucose control, especially after eating. Indeed, amylin has been shown to have at least two effects believed to be important for normal glucose metabolism: it slows glucose inflow into the bloodstream from the gastrointestinal tract, and it suppresses glucagon secretion and thereby helps to lower glucose production by the liver.

After a typical meal, over 75 grams of glucose pass from the stomach and gastrointestinal tract, through the bloodstream, and into muscle and liver tissue for storage as glycogen. This amount of glucose is large relative to the five to six grams of glucose typically present at normal concentrations in the blood pool of an average adult. In healthy people, the rate of glucose inflow from the gastrointestinal tract is closely matched with the rate of outflow into the storage tissues, allowing the body to maintain normal blood glucose concentrations. The endocrine regulator of glucose outflow rate is insulin, which is secreted by pancreatic beta-cells in response to rising blood glucose concentrations. The endocrine regulator of glucose inflow rate has, until recently, been unknown.

Now, preclinical and clinical data have confirmed the role of amylin as a key regulator of glucose inflow rate. In animals and humans, rising amylin blood concentrations slow down the transfer of nutrients from the stomach to the intestines. Young et al., *Diabetalogia* 38:642–648 (1995); Young et al., *Metabolism* 45:1–3 (1996); Macdonald et al., *Diabetalogia* 38(supp 1):A32 (1995). This transfer is the rate-limiting step in the appearance of nutrient-derived glucose in the bloodstream. Thus, the simultaneous secretion of both insulin and amylin by the pancreatic beta-cells acts to regulate both inflow and outflow, thereby keeping post-meal blood glucose concentrations within a narrow and healthy range.

Between meals, the liver produces glucose which is carried by the bloodstream to the brain and other tissues that do not store glucose. The endocrine regulator of liver glucose production is glucagon, a peptide hormone secreted by pancreatic alpha-cells in response to falling blood glucose concentrations. At mealtime, glucagon secretion must be suppressed to avoid hyperglycemia induced by excess liver glucose production, and a known regulator of glucagon suppression is insulin. Other preclinical and clinical data support the idea that amylin too is an endocrine regulator of glucagon secretion. In animals and humans, increasing amylin blood concentrations slows pancreatic alpha-cell secretion of glucagon, an effect which amplifies the same regulatory effect of insulin. Gedulin et al., *Metabolism* 46:67–70 (1997). Thus, the simultaneous secretion of both insulin and amylin by the pancreatic beta-cells can act to suppress glucagon and curtail liver glucose production, thereby helping to keep post-meal blood glucose concentrations within a narrow and healthy range.

The use of amylin and other amylin agonists for the treatment of diabetes mellitus is the subject of U.S. Pat. No. 5,175,145, issued Dec. 29, 1992. Pharmaceutical compositions containing amylin and amylin plus insulin are described in U.S. Pat. No. 5,124,314, issued Jun 23, 1992.

One amylin agonist, pramlintide ($^{25,28,29}$Pro-human amylin, also previously referred to as "AC137"), a synthetic analog of human amylin in which select modifications have been made, is presently undergoing testing in people with Type 1 and Type 2 diabetes who use insulin to control their blood glucose. To confirm that replacing the desired biological actions of amylin, along with insulin, is beneficial compared to the use of insulin alone, Amylin Pharmaceuticals, Inc. (San Diego, Calif.) has conducted extensive preclinical and clinical studies of pramlintide, including eighteen Phase I and II clinical trials involving over 1,000 people with diabetes who use insulin. In seven-out-of-seven Phase II studies assessing glucose control, this amylin agonist analogue caused a statistically significant and clinically relevant reduction in blood glucose. These seven studies evaluated a progression of different endpoint assessments of glucose control including reduction in post-meal glucose concentrations, 24-hour average glucose concentrations, and fructosamine concentrations. Fructosamine is a surrogate marker which reflects average glucose concentrations over the two-to-three weeks prior to testing. Pramlintide has been well tolerated at anticipated therapeutic doses and there have been no clinically important safety concerns. Pramlintide is the subject of U.S. Pat. No. 5,686,411, issued Nov. 11, 1997.

Specifically, in a 14-day, double-blind, placebo-controlled Phase II clinical study completed in 1994, subjects with Type 1 diabetes had a statistically significant reduction in blood-glucose concentrations after a test meal compared to placebo when they self injected pramlintide three times per day in addition to their usual insulin therapy. Results from this study were published in April 1996 in *Diabetologia*.

In January 1995, results from a placebo-controlled, double-blind, clinical pharmacology study were reported, showing that an intravenous infusion of pramlintide significantly reduced post-meal blood-glucose concentrations in subjects with Type 2 diabetes who use insulin. This finding was similar to previous observations in comparable studies in people with Type 1 diabetes.

Results from this study were presented at the June 1995 annual meeting of the American Diabetes Association and the September 1995 annual meeting of the European Association for the Study of Diabetes.

In February 1995, results from another 14-day, double-blind, placebo-controlled Phase II study in subjects with Type 1 diabetes were reported, which showed that 30-microgram doses of pramlintide self-administered four times per day resulted in a statistically significant reduction in blood-glucose concentrations following a test meal and also significantly reduced the average blood-glucose concentrations over a 24-hour observation period (35 mg/dl, p=0.003) during which patients ingested their usual meals, compared to placebo. Results from this study were presented at the September 1995 annual meeting of the European Association for the Study of Diabetes.

In August 1995, results from a 28-day, double-blind, placebo-controlled Phase II trial in subjects with Type 1 diabetes were reported. This study showed that self-administered, 30-microgram doses of pramlintide four times per day (one before each main meal and a late-night snack) significantly lowered the excessive rise in post-meal blood-glucose concentration, compared to the placebo control group. Using this dosing regimen, the study also confirmed that pramlintide significantly lowered 24-hour average blood-glucose concentrations (31 mg/dl, p=0.009) and fructosamine (33 micromoles/liter, p=0.003), compared to placebo. As in previous studies, the 30-microgram dose of pramlintide was well tolerated. The only adverse effects significantly different from those reported by the placebo group were mild gastrointestinal symptoms in a small number of patients, and those were substantially reduced after the first two weeks of treatment. Results from this study were presented at the June 1996 annual meeting of the American Diabetes Association. At the same meeting, abstracts were presented indicating that it is feasible to mix pramlintide with Humulin® 70/30 insulin in the same syringe just prior to administration. In this study involving people with Type 1 diabetes, plasma glucose profiles were similar when identical doses of Humulin 70/30 insulin and pramlintide were administered, either as separate injections or mixed in the same syringe immediately prior to injection.

In August 1996, the results of a 28-day, double-blind, placebo-controlled Phase II trial in subjects with Type 2 diabetes who use insulin were also reported. In all dose groups, self-administered pramlintide significantly lowered fructosamine as follows: 30 micrograms four times a day (17.5 micromoles/liter, p=0.029), 60 micrograms four times a day (22.6 micromoles/liter, p=0.001), and 60 micrograms three times a day (24.1 micromoles/liter, p=0.003). These results are similar to the positive findings previously reported in patients with Type 1 diabetes. The reduction in fructosamine in the 60 microgram dose groups represents a 50 to 60% reduction in the excess of fructosamine above the upper limits of the normal range. Therefore, this study demonstrated that three-times-a-day dosing of pramlintide can achieve similar clinical benefits as four-times-a-day dosing in people with Type 2 diabetes who use insulin. The study also corroborated the excellent short-term safety profile that had been observed to date in other clinical trials of pramlintide.

As a result of pioneering work with amylin and the invention of superior agonist analogues of amylin by Amylin Pharmaceuticals, Inc., the use of amylin and agonists of amylin show great therapeutic promise. Now, however, as set forth in the following detailed description of the invention, still further surprising new discoveries and inventions comprising synergistic compositions that include certain insulins and amylin agonist compounds have been made which will help people with diabetes improve their glucose control without imposing unacceptable treatment burdens.

SUMMARY OF THE INVENTION

We have discovered, surprisingly, that amylin agonists, for example, the amylin agonist analog $^{25,28,29}$Pro-h-amylin (also known as "pramlintide" and previously referred to as "AC-0137"), can be mixed with an intermediate-acting insulin zinc suspension or protamine zinc insulin, for example, lente insulin or NPH insulin, to provide an amylin agonist, or an amylin, with a longer duration of action. Administration of this mixture to people who use insulin to control their blood glucose provides a long-acting glucose lowering effect, and can obviate the need for one or more insulin and/or amylin or agonist injections normally administered, for example, prior to the second meal of the day.

In one aspect then, the present invention is directed to novel pharmaceutical mixtures of amylin agonists or amylins and intermediate-acting insulins. These pharmaceuticals have unique attributes when used to treat people with diabetes. As described more fully herein, this amylin agonist/intermediate-acting insulin mixture leads to a glucose lowering effect of greater magnitude and longer duration in comparison to the glucose lowering effects of equivalent amounts of these drugs administered separately.

The invention also includes methods for treating people who use insulin to control their blood glucose which comprises the administration of an amylin agonist, for example, the amylin agonist analog $^{25,28,29}$Pro-h-amylin, or an amylin, that has been mixed together with an intermediate-acting insulin (or any insulin preparation which contains an intermediate-acting insulin) in a single injection. By "intermediate-acting insulin" is meant an insulin formulated as an insulin zinc suspension or as a modified protamine zinc insulin suspension that is crystalline, preferably having a pH of from about 7.0 to about 7.4, more preferably a pH of about 7.2. Examples of preferred intermediate acting insulins include Eli Lilly's & Company's Humulin N® (human insulin (recombinant DNA origin) isophane suspension), NPH Iletin® I (isophane insulin suspension, USP, beef-pork), NPH Iletin® II (isophane insulin suspension, USP, purified pork), and Novo Nordisk's Novolin® N (NPH, human insulin isophane suspension (recombinant DNA origin)) and NPH Purified. Pork Isophane Insulin Suspension USP (100 units/ml). Other intermediate acting insulins include Eli Lilly's & Company's Humulin® L (lente; human insulin (rDNA origin) zinc suspension, 100 Units), Lente® Iletine I, (insulin zinc suspension, beef-pork), Lente Iletin® II (insulin zinc suspension, purified pork), and Novo Nordisk's Novolin® L (Lente, Human Insulin Zinc Suspension (recombinant DNA origin), 100 Units/ml) and Lente Purified Pork Insulin (Zinc Suspension, USP 100 Units/ml). Still other intermediate-acting insulins available from Eli Lilly include Humulin® 50/50 (50% human insulin isophane suspension and 50% human insulin injection (rDNA origin), 100 Units); Humulin® 70/30 (70% human insulin isophane suspension and 30% human insulin injection (rDNA origin), 100 Units); Intermediate-acting insulins available from Novo Nordisk include Novolin® 70/30 (70% NPH, Human Insulin Isophane Suspension and 30% Regular, Human Insulin Injection (recombinant DNA origin), 100 Units/ml).]

The term "amylin" is understood to include compounds such as those defined in U.S. Pat. No. 5,234,906, issued Aug. 10, 1993, for "Hyperglycemic Compositions," and U.S. Pat. No. 5,367,052, issued Nov. 22, 1994 for "Amylin Peptides," the contents of which are hereby incorporated by reference. For example, it includes the human peptide hormone referred to as amylin and secreted from the beta cells of the pancreas, and species variations of it. "Amylin agonist" is also a term known in the art, and refers to a compound which mimics effects of amylin. An amylin agonist may be a peptide or a non-peptide compound, and includes amylin agonist analogs.

The term "amylin agonist analog" is understood to refer to derivatives of an amylin which act as amylin agonists, normally, it is presently believed, by virtue of binding to or otherwise directly or indirectly interacting with an amylin receptor or other receptor or receptors with which amylin itself may interact to elicit a biological response. Amylin agonist analogs include those described and claimed in U.S. Pat. No. 5,686,411, entitled "Amylin Agonist Peptides And Uses Therefor," the contents of which is also hereby incorporated by reference. In a preferred embodiment, the amylin agonist is an amylin agonist analog, preferably, $^{25,28,29}$Pro-h-amylin.

In one aspect, the invention is directed to a method of treating an insulin-using mammalian subject comprising administering together to said subject effective glucose-lowering amounts of an amylin, preferably an amylin agonist having superior physicochemical and other properties compared to those of human amylin, such as pramlintide, and an intermediate-acting insulin. By "effective glucose-lowering amount" is meant an amount effective to reduce or normalize glucose.

In another aspect, the invention is directed to a method of enhancing the glucose-lowering activity of an intermediate-acting insulin comprising administering said intermediate-acting insulin along with an amylin, preferably an amylin agonist having superior physicochemical and other properties compared to those of human amylin, such as pramlintide, as described herein. This co-administration enables the use of lower and less frequent doses of either or both drugs with a concomitant reduction in the risk of possible side effects. Such co-administration is performed by drawing such same container for administration together. In a preferred embodiment, the amylin agonist is an amylin agonist analog, preferably, pramlintide, and the container is a syringe.

In a related aspect, the invention features pharmaceutical compositions comprising a therapeutically effective amount of a mixture of (1) an amylin agonist as described herein, preferably, the amylin agonist analog, pramlintide, or an amylin and (2) an intermediate-acting insulin, preferably an NPH insulin. Such compositions may include pharmaceutically acceptable salts of an amylin agonist or an amylin, and/or pharmaceutically acceptable salts of an intermediate-acting insulin. Such compositions may further comprise a pharmaceutically acceptable carrier.

BRIEF DESCRIPTION OF THE DRAWINGS

FIG. 13 shows plasma glucose concentrations after subcutaneous administration of pramlintide combined with NPH and regular insulin (PRAM+NPH+R mixed) compared to administration of pramlintide, NPH insulin, and regular insulin in separate injections in patients with Type I diabetes mellitus (Mean±SEM; N=30).

FIG. 14 shows plasma glucose concentrations after subcutaneous administration of pramlintide combined with NPH and regular insulin (PRAM+NPH+R mixed) compared to administration of placebo combined with NPH and regular insulin (PBO+NPH+R mixed) in patients with Type I diabetes mellitus (Mean±SEM; N=30)

DETAILED DESCRIPTION OF THE INVENTION

Figure 1:
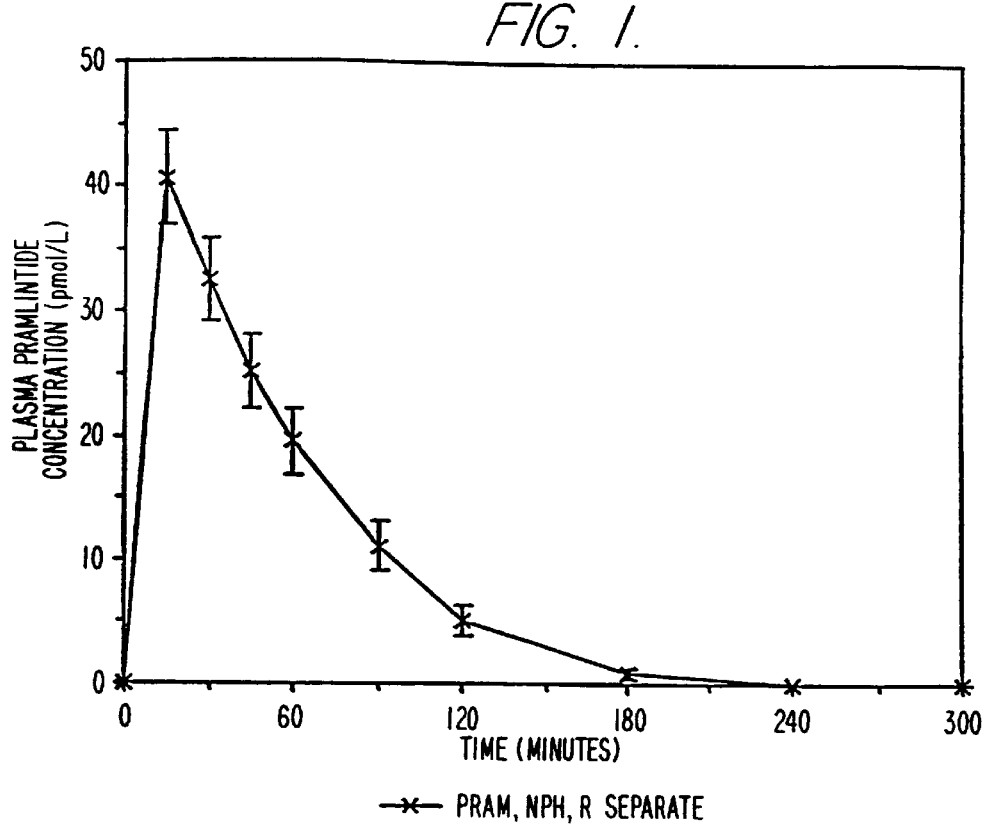
FIG. 1 shows plasma pramlintide concentrations after subcutaneous administration of pramlintide, NPH insulin, and regular insulin in separate injections in patients with Type I diabetes mellitus (Mean±SEM; N=29)

It has now been demonstrated that amylin agonist peptides can be formulated as described herein and in an application filed concurrently herewith entitled "Formulations for Amylin Agonist Peptides," the contents of which are hereby incorporated in their entirety by reference, to yield a compatible insulin/amylin agonist or amylin peptide pharmaceutical having superior glucose lowering properties when compared to insulin alone and when compared to insulin and an amylin agonist or amylin peptide administered separately. As shown by the clinical trial results described in Examples 1 and 2, which involved the amylin agonist peptide pramlintide, when mixed with an intermediate-acting insulin, such as NPH insulin or isophane insulin, amylin agonist peptides are rapidly absorbed and eliminated following administration of agonist peptide, regular insulin, and NPH insulin administered as separate and in various combined subcutaneous injections. Additionally, when mixed with an intermediate-acting insulin, such as NPH or isophane insulin, amylin agonist peptides have increased bioavailability compared to other treatments as evidenced by increased values for $AUC_{(0-300)}$. Additionally, the clinical results described herein demonstrate that there is an increase in median insulin $C_{max}$ associated with mixing an amylin agonist peptide according to the present invention with regular and/or an intermediate-acting insulin, such as NPH insulin or isophane insulin, compared to administration in separate injections. The increase in median $C_{max}$ is greatest when the amylin agonist peptide is mixed with the intermediate-acting insulin. There is also a delay in median insulin $T_{max}$ which is greatest when an amylin agonist peptide, regular insulin, and an intermediate-acting insulin are all mixed in the same syringe prior to injection. Furthermore, equivalence in insulin $AUC_{(0-600)}$ has been demonstrated for an amylin agonist peptide mixed with regular insulin and/or an intermediate-acting insulin compared to administration in separate injections, and when the amylin agonist peptide is mixed with an intermediate-acting insulin in one syringe and regular insulin is administered by separate injection, insulin has increased bioavailability compared to other treatments between 0 and 300 minutes.

The results of the clinical trials described in Examples 1 and 2 also demonstrate that there is a decrease in median glucose $C_{max}$ values associated with mixing an amylin agonist peptide according to the present invention with NPH insulin compared to administration in separate injections. For example, when an intermediate-acting insulin, NPH insulin, was administered in a separate injection from an amylin agonist peptide, pramlintide, a higher glucose peak was observed after lunch than when the intermediate-acting insulin was administered in the same syringe with pramlintide. Additionally, when an intermediate-acting insulin was administered in the same syringe with an amylin agonist peptide, median glucose $C_{max}$ values were lower. The results also demonstrated that over the entire time period (0 to 600 minutes) the glucose profile was clinically optimal with the combination of an amylin agonist peptide and an intermediate-acting insulin in one syringe with or without regular insulin compared to the other treatments.

The evaluation of AUC, $C_{max}$, and $T_{max}$ values determined from plasma glucose concentrations during the breakfast period (0 to 300 minutes after dosing) and during the lunch period (300 to 600 minutes after dosing) support the same conclusions as those drawn from the 0 to 600 minute data. Data regarding plasma glucose during the breakfast period showed that median glucose $AUC_{(0-300)}$, $C_{max}$, and $T_{max}$ values are comparable for an amylin agonist mixed with regular and/or and intermediate-acting insulin (e.g., NPH insulin and isophane insulin) compared to administration in separate injections. Thus, in Example 1, median glucose $C_{max}$ values were lower, and between treatment comparisons for glucose $C_{max}$ were statistically significant.

The data for plasma glucose during the lunch period demonstrated equivalence in glucose $AUC_{(300-600)}$ values following administration of an amylin agonist peptide mixed with regular insulin without an intermediate-acting insulin compared to administration in separate injections. Additionally, median glucose $AUC_{(300-600)}$ values following administration of an amylin agonist peptide mixed with an intermediate-acting insulin were lower compared to administration in separate injections. Importantly, after lunch, a lower glucose peak was observed for both treatments when an amylin agonist and an intermediate-acting insulin were mixed than when an intermediate-acting insulin was administered in a separate injection.

In sum, it has now been discovered that an amylin agonist can be mixed according to the present invention with a regular insulin and/or an intermediate-acting insulin (e.g., NPH insulin and/or iosphane insulin) prior to injection; and, importantly that there is an advantage, with respect to lowered and extended glucose control, to mixing an amylin agonist (e.g., pramlintide) and an intermediate-acting insulin prior to injection. This invention will allow patients to administer insulin and an amylin agonist or amylin less frequently and with fewer injections.

Amylin agonists useful in this invention include amylin agonist analogs disclosed and claimed in the above-noted U.S. Pat. No. 5,686,411, entitled "New Amylin Agonist Peptides And Uses Therefor." Preferred amylin agonist analogs include $^{25,28,29}$Pro-h-amylin, $^{18}$Arg$^{25,28,29}$Pro-h-amylin, and $^{18}$Arg$^{25,28}$Pro-h-amylin.

Activity as amylin agonists can be confirmed and quantified by performing various screening assays, including the nucleus accumbens receptor binding assay described below in Example 6, followed by the soleus muscle assay described below in Example 7, a gastric emptying assay described below in Example 8 or 9, or by the ability to induce hypocalcemia or reduce postprandial hyperglycemia in mammals, as described herein.

The receptor binding assay, a competition assay which measures the ability of compounds to bind specifically to membrane-bound amylin receptors, is described in U.S. Pat. No. 5,264,372, issued Nov. 23, 1993, the disclosure of which is incorporated herein by reference. The receptor binding assay is also described in Example 6 below. A preferred source of the membrane preparations used in the assay is the basal forebrain which comprises membranes from the nucleus accumbens and surrounding regions. Compounds being assayed compete for binding to these receptor preparations with $^{125}$I Bolton Hunter rat amylin. Competition curves, wherein the amount bound (B) is plotted as a function of the log of the concentration of ligand are analyzed by computer, using analyses by nonlinear regression to a 4-parameter logistic equation (Inplot program; GraphPAD Software, San Diego, Calif.) or the ALLFIT program of DeLean et al. (ALLFIT, Version 2.7 (NIH, Bethesda, Md. 20892)). Munson and Rodbard, *Anal. Biochem.* 107:220–239 (1980).

Assays of biological activity of amylin agonists in the soleus muscle may be performed using previously described methods (Leighton, B. and Cooper, *Nature*, 335:632–635 (1988); Cooper, et al., *Proc. Natl. Acad. Sci. USA* 85:7763–7766 (1988)), in which amylin agonist activity may be assessed by measuring the inhibition of insulin-stimulated glycogen synthesis. The soleus muscle assay is also described below.

Methods of measuring the rate of gastric emptying are disclosed in, for example, Young et al., *Diabetolocia*, 38(6): 642–648 (1995). In a phenol red method, which is described below, conscious rats receive by gavage an acoloric gel containing methyl cellulose and a phenol red indicator. Twenty minutes after gavage, animals are anesthetized using halothane, the stomach exposed and clamped at the pyloric and lower esophageal sphincters, removed and opened into an alkaline solution. Stomach content may be derived from the intensity of the phenol red in the alkaline solution, measured by absorbance at a wavelength of 560 nm. In a tritiated glucose method, which is described in Example 9 below, conscious rats are gavaged with tritiated glucose in water. The rats are gently restrained by the tail, the tip of which is anesthetized using lidocaine. Tritium in the plasma separated from tail blood is collected at various timepoints and detected in a beta counter. Test compounds are normally administered about one minute before gavage.

Effects of amylin agonists or amylins can be identified, evaluated, or screened for using the methods described below, or other art-known or equivalent methods for determining glucose lowering effect. Preferred amylin agonist compounds exhibit activity in the receptor binding assay on the order of less than about 1 to 5 nM, preferably less than about 1 nM and more preferably less than about 50 pM. In the soleus muscle assay, preferred amylin agonist compounds show $EC_{50}$ values on the order of less than about 1 to 10 micromolar. In the gastric emptying assays, preferred agonist compounds show $ED_{50}$ values on the order of less than 100 μg/rat.

Amylin and peptide amylin agonists may be prepared using standard solid-phase peptide synthesis techniques and preferably an automated or semiautomated peptide synthesizer, taking care to use appropriate reactants and conditions to ensure that any amylin or amylin agonist analogue is prepared to include a C-terminal amide (typically in the form of a tyrosinamide residue) and to include a bridge between the residues normally found at positions 2 and 7 (typically a disulfide bridge between the cysteine amino acids found at these positions), both of which are required for full biological activity. Typically, using such techniques, an α-N-carbamoyl protected amino acid and an amino acid attached to the growing peptide chain on a resin are coupled at room temperature in an inert solvent such as dimethylformamide, N-methylpyrrolidinone or methylene chloride in the presence of coupling agents such as dicyclohexylcarbodiimide and 1-hydroxybenzotriazole in the presence of a base such as diisopropylethylamine. The α-N-carbamoyl protecting group is removed from the resulting peptide-resin using a reagent such as trifluoroacetic acid or piperidine, and the coupling reaction repeated with the next desired N-protected amino acid to be added to the peptide chain. Suitable N-protecting groups are well known in the art, with t-butyloxycarbonyl (tBoc) and fluorenylmethoxycarbonyl (Fmoc) being preferred herein.

The solvents, amino acid derivatives and 4-methylbenzhydryl-amine (Rink) resin used in the peptide synthesizer may be purchased from Applied Biosystems Inc. (Foster City, Calif.). The following side-chain protected amino acids may be purchased from Applied Biosystems, Inc.: Boc-Arg(Mts), Fmoc-Arg(Pmc), Boc-Thr(Bzl), Fmoc-Thr(t-Bu), Boc-Ser(Bzl), Fmoc-Ser(t-Bu), Boc-Tyr(BrZ), Fmoc-Tyr(t-Bu), Boc-Lys(Cl-Z), Fmoc-Lys(Boc), Boc-Glu (Bzl), Fmoc-Glu(t-Bu), Fmoc-His(Trt), Fmoc-Asn(Trt), and Fmoc-Gln(Trt). Boc-His(BOM) may be purchased from Applied Biosystems, Inc. or Bachem Inc. (Torrance, Calif.). Anisole, dimethylsulfide, methylsulfide, phenol, ethanedithiol, and thioanisole may be obtained from Aldrich Chemical Company (Milwaukee, Wis.). Air Products and Chemicals (Allentown, Pa.) supplies HF. Ethyl ether, acetic acid and methanol may be purchased from Fisher Scientific (Pittsburgh, Pa.).

Solid phase peptide synthesis may be carried out with an automated peptide synthesizer (Model 430A, Applied Biosystems Inc., Foster City, Calif.) using the NMP/HOBt (Option 1) system and Tboc or Fmoc chemistry (see, Applied Biosystems User's Manual for the ABI 430A Peptide Synthesizer, Version 1.3B Jul. 1, 1988, section 6, pp. 49–70, Applied Biosystems, Inc., Foster City, Calif.) with capping. Boc-peptide-resins may be cleaved with HF (−5° C. to 0° C., 1 hour). The peptide may be extracted from the resin with alternating water and acetic acid, and the filtrates lyophilized. The Fmoc-peptide resins may be cleaved according to standard methods (*Introduction to Cleavage Techniques*, Applied Biosystems, Inc., 1990, pp. 6–12). Peptides may be also be assembled using an Advanced Chem Tech Synthesizer (Model MPS 350, Louisville, Ky.).

Peptides may be purified by RP-HPLC (preparative and analytical) using a Waters Delta Prep 3000 system. A C4, C8 or C18 preparative column (10 F, 2.2×25 cm; Vydac, Hesperia, Calif.) may be used to isolate peptides, and purity may be determined using a C4, C8 or C18 analytical column (5 F, 0.46×25 cm; Vydac). Solvents (A=0.1% TFA/water and B=0.1% TFA/CH$_3$CN) may be delivered to the analytical column at a flowrate of 1.0 ml/min and to the preparative column at 15 ml/min. Amino acid analyses may be performed on the Waters Pico Tag system and processed using the Maxima program. Peptides may be hydrolyzed by vapor-phase acid hydrolysis (115° C., 20–24 h). Hydrolysates may be derivatized and analyzed by standard methods (Cohen, et al., *The Pico Tag Method: A Manual of Advanced Techniques for Amino Acid Analysis*, pp. 11–52, Millipore Corporation, Milford, Mass. (1989)). Fast atom bombardment analysis may be carried out by M-Scan, Incorporated (West Chester, Pa.). Mass calibration may be performed using cesium iodide or cesium iodide/glycerol. Plasma desorption ionization analysis using time of flight detection may be carried out on an Applied Biosystems Bio-Ion 20 mass spectrometer.

Peptide compounds useful in the invention may also be prepared using recombinant DNA techniques, using methods now known in the art. See, e.g., Sambrook et al., *Molecular Cloning: A Laboratory Manual*, 2d Ed., Cold Spring Harbor (1989). Non-peptide compounds useful in the present invention may be prepared by art-known methods.

The compounds referenced above may form salts with various inorganic and organic acids and bases. Such salts include salts prepared with organic and inorganic acids, for example, HCl, HBr, H$_2$SO$_4$, H$_3$PO$_4$, trifluoroacetic acid, acetic acid, formic acid, methanesulfonic acid, toluenesulfonic acid, maleic acid, fumaric acid and camphorsulfonic acid. Salts prepared with bases include ammonium salts, alkali metal salts, e.g., sodium and potassium salts, and alkali earth salts, e.g., calcium and magnesium salts. Acetate, hydrochloride, and trifluoroacetate salts are preferred. The salts may be formed by conventional means, as by reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

Compositions useful in the invention may conveniently be provided in the form of formulations suitable for parenteral (including intravenous, intramuscular and subcutaneous) or nasal or oral administration. A suitable administration format may best be determined by a medical practitioner for each patient individually. Suitable pharmaceutically acceptable carriers and their formulation are described in standard formulation treatises, e.g., *Remington's Pharmaceutical Sciences* by E. W. Martin. See also Wang, Y. J. and Hanson, M. A. "Parenteral Formulations of Proteins and Peptides: Stability and Stabilizers," *Journal of Parenteral Science and Technology*, Technical Report No. 10, Supp. 42:2S (1988). Compounds provided as parenteral compositions for injection or infusion can, for example, be suspended in an inert oil, suitably a vegetable oil such as sesame, peanut, olive oil, or other acceptable carrier. These compositions may be sterilized by conventional sterilization techniques, or may be sterile filtered. The compositions may contain pharmaceutically acceptable auxiliary substances as required to approximate physiological conditions, such as pH buffering agents. Useful buffers include for example, sodium acetate/acetic acid buffers. A form of repository or "depot" slow release preparation may be used so that therapeutically effective amounts of the preparation are delivered into the bloodstream over many hours or days following transdermal injection or delivery.

Preferably, these parenteral dosage forms are prepared according to the concurrently filed application, "Formulations for Amylin Agonist Peptides," and include approximately 0.01 to 0.5% (w/v), respectively, of an amylin agonist, or amylin, as the active ingredient, in an aqueous system along with approximately 0.02 to 0.5%(w/v) of an acetate, phosphate, citrate or glutamate buffer to obtain a pH of the final composition of approximately 3.0 to 6.0 (more preferably 3.5 to 5.5, and most preferably 4.0), provided, however, that if the amylin or amylin agonist has physicochemical characteristics similar to those of human amylin, it should be formulated and lyophilized for storage (and used immediately following reconstitution) as compounds such as human amylin are poorly soluble and highly unstable. The desired isotonicity may be accomplished using polyols (for example, mannitol and sorbitol) sodium chloride or other pharmaceutically acceptable agents such as dextrose, boric acid, sodium tartrate, propylene glycol, or other inorganic or organic solutes. Mannitol is preferred, and at 1.0 to 10.0% (w/v). Approximately 0.005 to 1.0% (w/v) of an antimicrobial preservative selected from the group consisting of m-cresol, benzyl alcohol, methyl, ethyl, propyl and butyl parabens and phenol is also present in the preferred formulation of product designed to allow the patient to withdraw multiple doses, but is not required for single-use containers. A sufficient amount of water for injection is used to obtain the desired concentration of solution. Sodium chloride, as well as other excipients, may also be present, if desired. Such excipients, however, must maintain the overall stability of the amylin agonist peptide, or amylin. Most preferably, in the amylin agonist formulation for parenteral administration from a multiple use container, the tonicity agent is mannitol, the buffer is an acetate buffer, the preservative is approximately 0.1 to 0.3 w/v of m-cresol, and the pH is approximately 3.7 to 4.3, most preferably 4.0. Liquid formulations of the invention should be substantially isotonic. An isotonic solution may be defined as a solution that has a concentration of electrolytes, non-electrolytes, or a combination of the two that will exert equivalent osmotic pressure as that into which it is being introduced, here, for example in the case of parenteral injection of the formulation, a mammalian tissue. By "substantially isotonic" is meant within ±20% of isotonicity, preferably within ±10%. The formulated product is included within a container, typically, for example, a vial, cartridge, prefilled syringe or disposable pen.

If desired, solutions of the above compositions may be thickened with a thickening agent such as methyl cellulose. They may be prepared in emulsified form, either water in oil or oil in water. Any of a wide variety of pharmaceutically acceptable emulsifying agents may be employed including, for example, acacia powder, a non-ionic surfactant (such as a Tween), or an ionic surfactant (such as alkali polyether alcohol sulfates or sulfonates, e.g., a Triton).

Compositions useful in the invention are prepared by mixing the ingredients following generally accepted procedures. For example, the selected components may be simply mixed in a blender or other standard device to produce a concentrated mixture which may then be adjusted to the final concentration and viscosity by the addition of water or thickening agent and possibly a buffer to control pH or an additional solute to control tonicity.

For use by the physician, the compositions will be provided in dosage unit form containing an amount of an amylin or amylin agonist, for example, an amylin agonist analog compound which will be effective in one or multiple doses to control glucose at the selected level. Therapeutically effective amounts of an amylin or amylin agonist, such as an amylin agonist analog, for use in the control of glucose are those that decrease glucose. As will be recognized by those in the field, an effective amount of therapeutic agent will vary with many factors including the age and weight of the patient, the patient's physical condition, the action to be obtained and other factors.

The effective single, divided or continuous glucose-lowering doses of the compounds, for example, including pramlintide, $^{18}Arg^{25,28,29}$Pro-h-amylin and $^{18}Arg^{25,28}$Pro-h-amylin will typically be in the range of 0.01 or 0.03 to about 5 mg/day, preferably about 0.01 or 0.5 to 2 mg/day and more preferably about 0.01 or 0.1 to 1 mg/day, for a 70 kg patient, administered in a single, divided or continuous doses. The exact dose to be administered is determined by the attending clinician and is dependent upon a number of factors, including, those noted above. Administration may be by injection or infusion, preferably by subcutaneous or intramuscular injection. orally active compounds may be taken orally, however dosages should be increased 5–10 fold.

Generally, in treating diabetes or other conditions that would benefit from lowered glucose, the compounds of this invention may be administered to patients in need of such treatment in a dosage ranges similar to those given above, however, the compounds may be administered more frequently, for example, one, two, or three times a day or continuously.

To assist in understanding the present invention, the following Examples are included which describe the results of a series of clinical and other experiments. The experiments relating to this invention should not, of course, be construed as specifically limiting the invention and such variations of the invention, now known or later developed, which would be within the purview of one skilled in the art are considered to fall within the scope of the invention as described herein and hereinafter claimed.

EXAMPLE 1

This clinical trial was designed to evaluate syringe mixing of short-acting and/or intermediate-acting insulins and the amylin agonist pramlintide. Pramlintide was synthesized by standard solid phase peptide synthesis methods. Insulins were obtained from their manufacturers, as noted. The trial was conducted as an open-label, single-center, five-period, randomized, crossover study with 1-week washout periods between treatments to compare pharmacokinetic profiles for plasma pramlintide, serum free insulin, and plasma glucose after pramlintide, NPH insulin (Humulin® N), and regular insulin (Humulin® R) were mixed and administered together and as separate subcutaneous injections.

Patients with Type I diabetes mellitus who were using NPH and regular insulin were enrolled and randomized to receive each of the following five treatments administered subcutaneously in random sequence with 1-week washout periods between treatments:

1. Pramlintide in one syringe, regular insulin in another syringe, and NPH insulin in a third syringe [PRAM, NPH, R separate];
2. Pramlintide and regular insulin in one syringe and a separate injection of NPH insulin [PRAM+R mixed, NPH separate];
3. Pramlintide and NPH insulin in one syringe and a separate injection of regular insulin [PRAM+NPH mixed, R separate];
4. Pramlintide, NPH insulin, and regular insulin in a single injection [PRAM+NPH+R mixed]; and,
5. Placebo (matching pramlintide), NPH insulin, and regular insulin in a single injection [PBO+NPH+R mixed].

Treatments were administered in randomized sequence at approximately 7:00 AM (Time 0), 15 minutes prior to breakfast on study days separated by a one week washout period. (Time 0 minutes on all figures represents the time of study drug administration.) On dosing days, patients received each of five treatments containing pramlintide or placebo and NPH or regular insulin administered combined or as separate injections in randomized sequence. The pramlintide dose was 30 µg in all treatments containing pramlintide. Throughout the study period, patients maintained a stable diet and exercise program and continued to receive their usual regular and NPH insulin doses. All treatments were administered by subcutaneous injection into the anterior abdominal wall. All syringes, including mixed injections, were given to the patient for self-administration within 5 minutes of preparation. Blood samples for plasma pramlintide, serum free insulin, and plasma glucose concentrations were obtained at the following time points: 0 (pre-dose), 15, 30, 45, 60, 90, 120, 180 minutes (3 hours), 4, and 5 hours following administration of study drug on study days 2, 4, 6, 8, and 10. In addition, blood samples were collected at 6, 7, 8.5, and 10 hours after dosing on the same days for serum free insulin and plasma glucose concentrations. On each dosing day, identical meals (breakfast, lunch, and dinner) were eaten. Patients ate their standardized lunch at 12:15 PM, 15 minutes after collection of the 5-hour blood samples. There was no noontime administration of any study drug, including insulin. Within 30 minutes after dosing, patients ate their standardized dinner meal.

The following pharmacokinetic parameters were calculated from the plasma pramlintide, serum free insulin, and plasma glucose concentrations: $C_{max}$ (the peak concentration determined as the highest observed concentration during the blood sampling interval); $T_{max}$ (the blood sampling time at which $C_{max}$ occurred); and, $AUC_{(0-t)}$ (the area under the concentration-time profile determined using the trapezoidal rule, where t=300 minutes (5 hours) for plasma pramlintide and t=600 minutes (10 hours) for serum free insulin and plasma glucose. Glucose parameters also were calculated for the meal periods. The effect of meals on plasma glucose profiles was evaluated by calculating AUC, $C_{max}$, and $T_{max}$ values for the period that included breakfast (0 to 300 minutes) and the period that included lunch (300 to 600 minutes). Mean plasma pramlintide concentration-time profiles and pharmacokinetics are described and compared between treatments.

Mean plasma pramlintide concentration-time profiles for all evaluable patients after all pramlintide treatments are displayed in FIGS. 1–4. Mean plasma pramlintide concentrations following administration of pramlintide, NPH insulin, and regular insulin (PRAM, NPH, R separate) in separate syringes are displayed in FIG. 1. Following subcutaneous administration of pramlintide, NPH insulin, and regular insulin in separate syringes, the plasma concentration profiles indicate that mean plasma pramlintide concentrations increased rapidly, reached peak concentration at 15 minutes after dosing, and declined rapidly thereafter to approach baseline at approximately 240 minutes after dosing.

Figure 2:
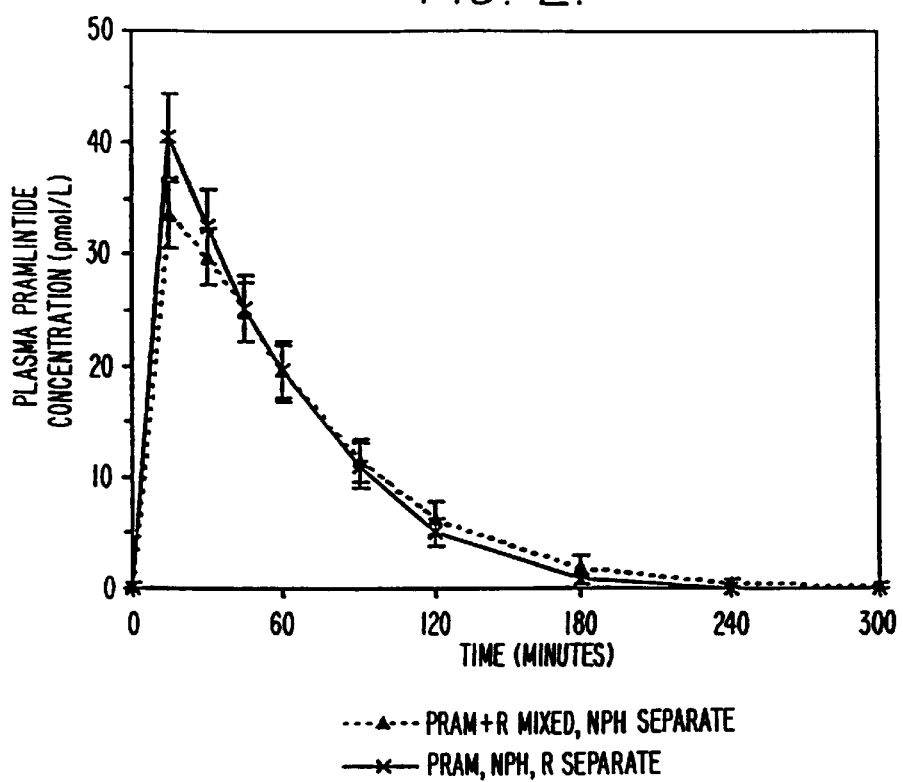
FIG. 2 shows plasma pramlintide concentrations after subcutaneous administration of pramlintide combined with regular insulin (Pram+R mixed, NPH separate) compared to administration of pramlintide, NPH insulin, and regular insulin in separate injections in patients with Type I diabetes mellitus (Mean±SEM; N=29).

Mean plasma pramlintide concentrations following administration of PRAM+R mixed, NPH separate compared to administration of PRAM, NPH, R separate are displayed in FIG. 2. The mean plasma pramlintide profile following administration of PRAM+R mixed, NPH separate was similar to that for PRAM, NPH, R separate. The mean plasma pramlintide profile for PRAM+R mixed, NPH separate exhibited a slightly lower peak concentration at 15 minutes, and then declined rapidly to approach baseline at 300 minutes after dosing.

Figure 3:
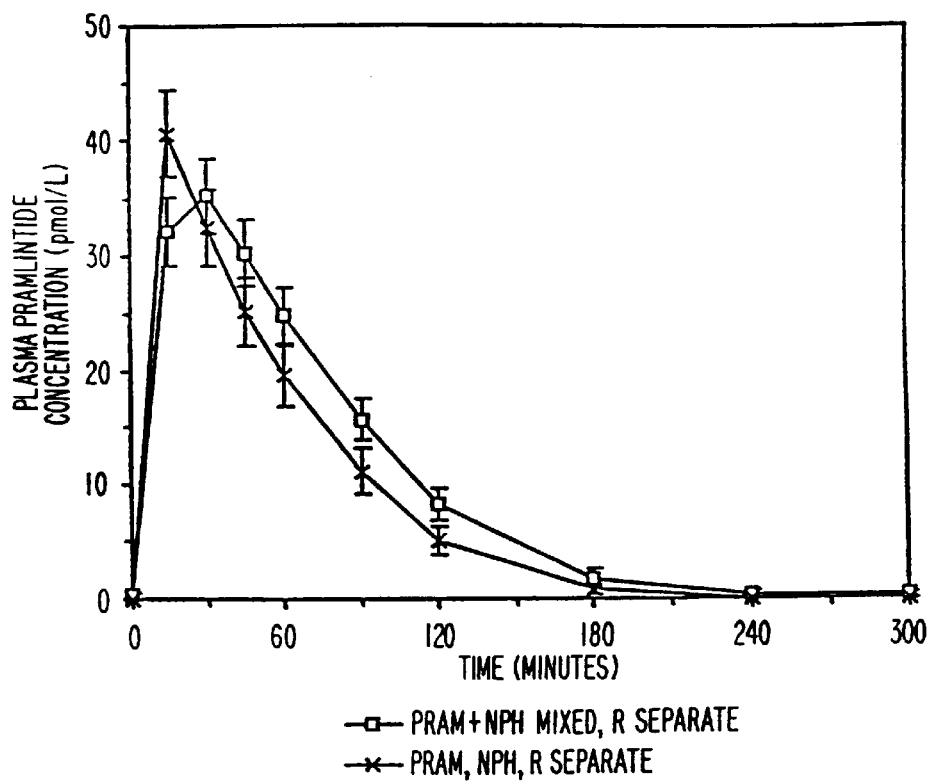
FIG. 3 shows plasma pramlintide concentrations after subcutaneous administration of pramlintide combined with NPH insulin (PRAM+NPH mixed, R separate) compared to administration of pramlintide, NPH insulin, and regular insulin in separate injections in patients with Type I diabetes mellitus (Mean±SEM; N=29)

Mean plasma pramlintide concentrations following administration of PRAM+NPH mixed, R separate compared to PRAM, NPH, R separate are displayed in FIG. 3. Following subcutaneous administration of PRAM+NPH mixed, R separate, mean plasma pramlintide concentrations increased with time, reached peak concentrations at 30 minutes after the dose, and declined rapidly thereafter to baseline at 300 minutes. Compared to PRAM, NPH, R separate, the mean peak concentration was reached later and was not as high, and the decline was not as rapid.

Figure 4:
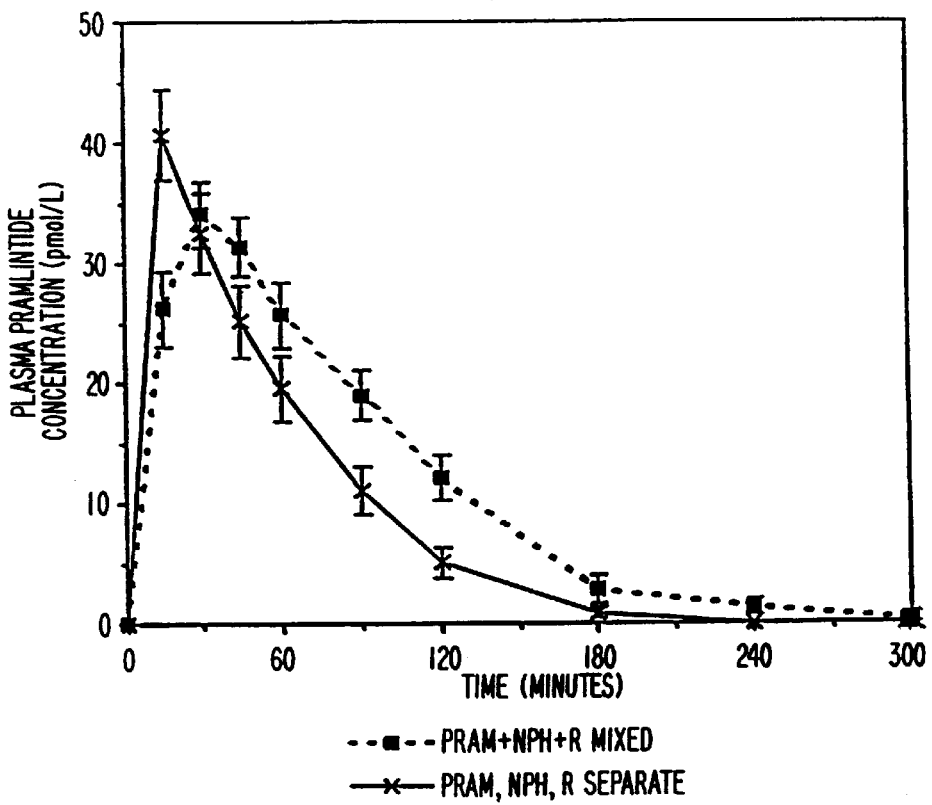
FIG. 4 shows plasma pramlintide concentrations after subcutaneous administration of pramlintide combined with NPH and regular insulin (PRAM+NPH+R mixed) compared to administration of pramlintide, NPH insulin, and regular insulin in separate injections in patients with Type I diabetes mellitus (Mean±SEM; N=29)
Figure 5:
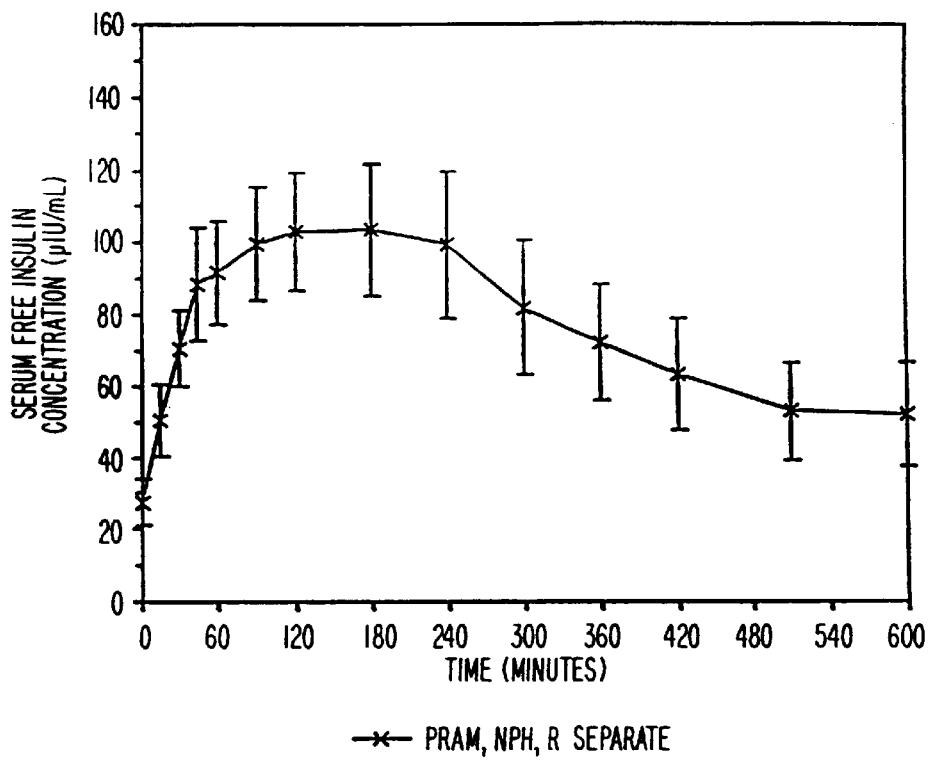
FIG. 5 shows serum free insulin concentrations after subcutaneous administration of pramlintide, NPH insulin, and regular insulin in separate injections in patients with Type I diabetes mellitus (Mean±SEM; N=30).

Mean plasma pramlintide concentrations following administration of PRAM+NPH+R mixed compared to PRAM, NPH, R separate are displayed in FIG. 4. The mean plasma pramlintide concentration profile after the administration of PRAM+NPH+R mixed increased with time, reached peak concentrations at 30 minutes after the dose, and declined rapidly thereafter to baseline at 300 minutes. Compared to PRAM, NPH, R separate, the mean peak concentration was reached later and was not as high, and the decline was not as rapid.

Mean±SEM plasma pramlintide pharmacokinetic parameter values for all evaluable patients following all pramlintide-containing treatments are displayed in the following Table 1.

TABLE 1

Plasma Pramlintide Pharmacokinetic Parameter Values in Patients with Type I Diabetes Mellitus Following Single Doses of Pramlintide, Regular Insulin, and NPH Insulin Administered as Separate and Combined Subcutaneous Injections [Mean ± SEM, Median, and Range]

| Treatment/ Statistics | $AUC_{(0-300)}$ (pmolCmin/L) | $C_{max}$ (pmol/L) | $T_{max}$ (min) |
|---|---|---|---|
| PRAM, NPH, R separate[a] | | | |
| N | 27 | 29 | 29 |
| Mean ± SEM | 2680.7 ± 308.5 | 42.3 ± 3.7 | 17.3 ± 1.0 |

TABLE 1-continued

Plasma Pramlintide Pharmacokinetic Parameter Values in Patients with Type I Diabetes Mellitus Following Single Doses of Pramlintide, Regular Insulin, and NPH Insulin Administered as Separate and Combined Subcutaneous Injections [Mean ± SEM, Median, and Range]

| Treatment/ Statistics | $AUC_{(0-300)}$ (pmolCmin/L) | $C_{max}$ (pmol/L) | $T_{max}$ (min) |
|---|---|---|---|
| Median | 2495.7 | 38.6 | 15 |
| Min–Max | 844.1–8052.0 | 10.9–105.2 | 14–30 |
| PRAM + R mixed, NPH separate[b] | | | |
| N | 27 | 29 | 29 |
| Mean ± SEM | 2693.31 ± 340.2 | 37.3 ± 3.0 | 22.6 ± 2.2 |
| Median | 2389.0 | 33.2 | 16 |
| Min–Max | 403.4–7824.2 | 10.0–71.4 | 14–60 |
| PRAM + NPH mixed, R separate[c] | | | |
| N | 27 | 29 | 29 |
| Mean ± SEM | 3120.1 ± 322.9 | 37.5 ± 3.1 | 27.9 ± 2.1 |
| Median | 3227.2 | 37.5 | 30 |
| Min–Max | 538.4–7062.7 | 10.7–77.1 | 14–60 |
| PRAM + NPH + R mixed[d] | | | |
| N | 27 | 29 | 29 |
| Mean ± SEM | 3516.7 ± 374.5 | 36.0 ± 2.8 | 32.4 ± 2.4 |
| Median | 2902.3 | 33.2 | 30 |
| Min–Max | 435.4–8133.3 | 10.1–69.1 | 15–60 |

[a]Pramlintide, NPH insulin, and regular insulin in separate syringes.
[b]Pramlintide + regular insulin in one syringe, with NPH insulin separate.
[c]Pramlintide + NPH insulin in one syringe, with regular insulin separate.
[d]Pramlintide + NPH insulin + regular insulin in one syringe.

These results demonstrate that when mixed with NPH insulin (PRAM+NPH mixed, R separate and PRAM+NPH+R mixed), pramlintide had increased bioavailability compared to the other treatments.

It can also be concluded with regard to pramlintide that: (1) pramlintide was rapidly absorbed and eliminated following administration of pramlintide, regular insulin, and NPH insulin administered as separate and in various combined subcutaneous injections; (2) there was a slight decrease in median pramlintide $C_{max}$ associated with mixing pramlintide with regular and/or NPH insulin compared to administration in separate injections; (3) there was a slight delay in median pramlintide $T_{max}$ when pramlintide was mixed with NPH insulin with and without regular insulin, and there was also a slight delay in mean pramlintide $T_{max}$ but not in median $T_{max}$ when pramlintide and regular insulin were combined and NPH insulin was separate; and (4) when mixed with NPH insulin, pramlintide had increased bioavailability compared to other treatments as evidenced by increased values for $AUC_{(0-300)}$.

Mean serum free insulin concentration-time profiles for all evaluable patients after all treatments are displayed in FIGS. 5–9. Mean serum free insulin concentrations following administration of PRAM, NPH, R separate are displayed in FIG. 5. Mean serum free insulin concentrations increased rapidly during the initial 45 minutes following administration PRAM, NPH, R separate.

Thereafter, mean serum free insulin concentrations continued to increase but at a slower rate until peak concentration was reached between 120 and 180 minutes. After the peak, mean serum free insulin concentrations declined slowly over the remainder of the 600-minute sampling period. At 600 minutes, the mean free insulin concentration remained above the mean baseline serum free insulin concentration.

Figure 6:
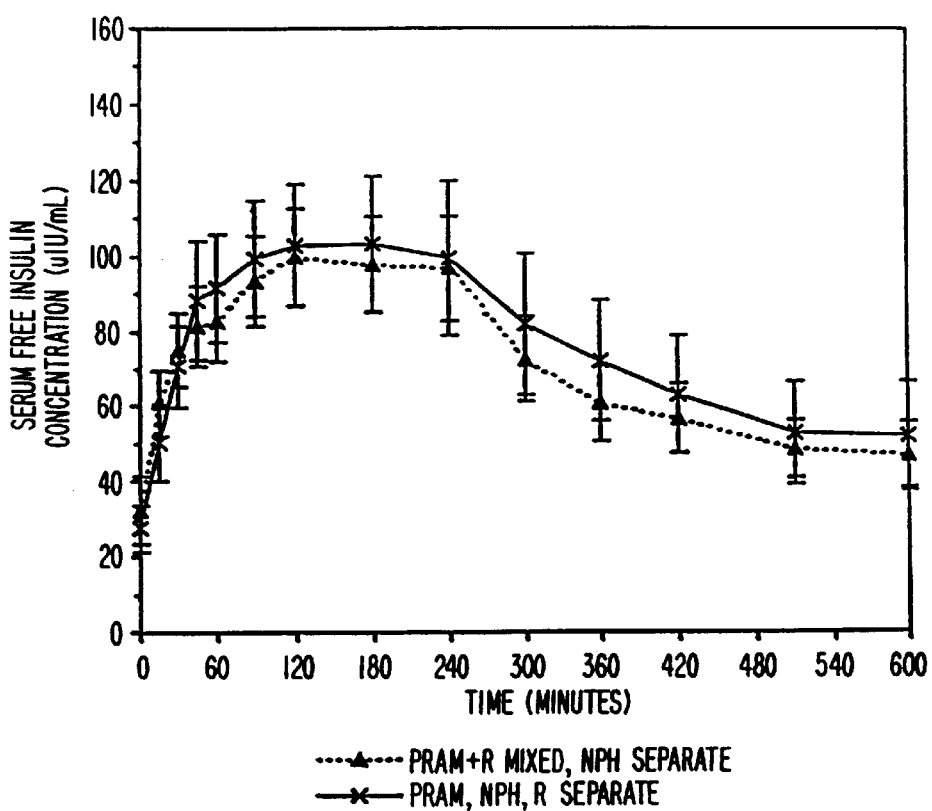
FIG. 6 shows serum free insulin concentrations after subcutaneous administration of pramlintide combined with regular insulin (PRAM+R mixed, NPH separate) compared to administration of pramlintide, NPH insulin, and regular insulin in separate injections in patients with Type I diabetes mellitus (Mean±SEM; N=30).

Mean serum free insulin concentrations following RAM+R mixed, NPH separate compared to PRAM, NPH, R separate are displayed in FIG. 6. The mean serum free insulin concentration-time profile following administration of PRAM+R mixed, NPH separate was similar to that for administration of PRAM, NPH, R separate. For both treatments, mean serum free insulin concentrations increased rapidly during the initial 45 minutes following administration and continued to increase but at a slower rate until peak concentration was reached at approximately 120 minutes after dosing. After the peak, mean serum free insulin concentrations remained flat until 240 minutes after which serum free insulin concentrations declined slowly over the remainder of the 600-minute sampling period. At 600 minutes, mean serum free insulin concentrations remained above the mean baseline serum free insulin concentrations.

Figure 7:
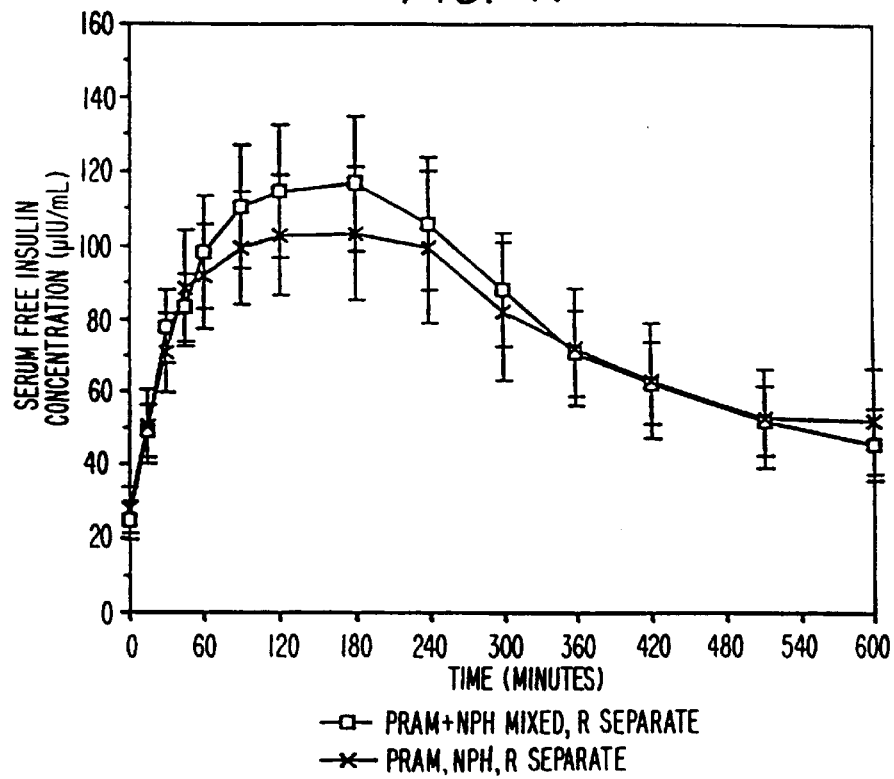
FIG. 7 shows serum free insulin concentrations after subcutaneous administration of pramlintide combined with NPH insulin (PRAM+NPH mixed, R separate) compared to administration of pramlintide, NPH insulin, and regular insulin in separate injections in patients with Type I diabetes mellitus (Mean±SEM; N=30).

Mean serum free insulin concentrations following PRAM+NPH mixed, R separate compared to PRAM, NPH, R separate are displayed in FIG. 7. Mean serum free insulin concentrations following administration of PRAM+NPH mixed, R separate increased rapidly during the initial 45 minutes similar to PRAM, NPH, R separate. However, the mean serum free insulin concentrations continued to increase after 45 minutes more rapidly to reach a higher mean peak concentration at approximately 180 minutes compared to that reached at 120 minutes for PRAM, NPH, R separate. Following the peak, mean serum free insulin concentrations remained higher than those for PRAM, NPH, R separate between 180 and 300 minutes. Thereafter, concentrations declined at a similar rate. At 600 minutes, the mean serum free insulin concentration remained above the mean baseline serum free insulin concentration but was similar to that observed with PRAM, NPH, R separate.

Figure 8:
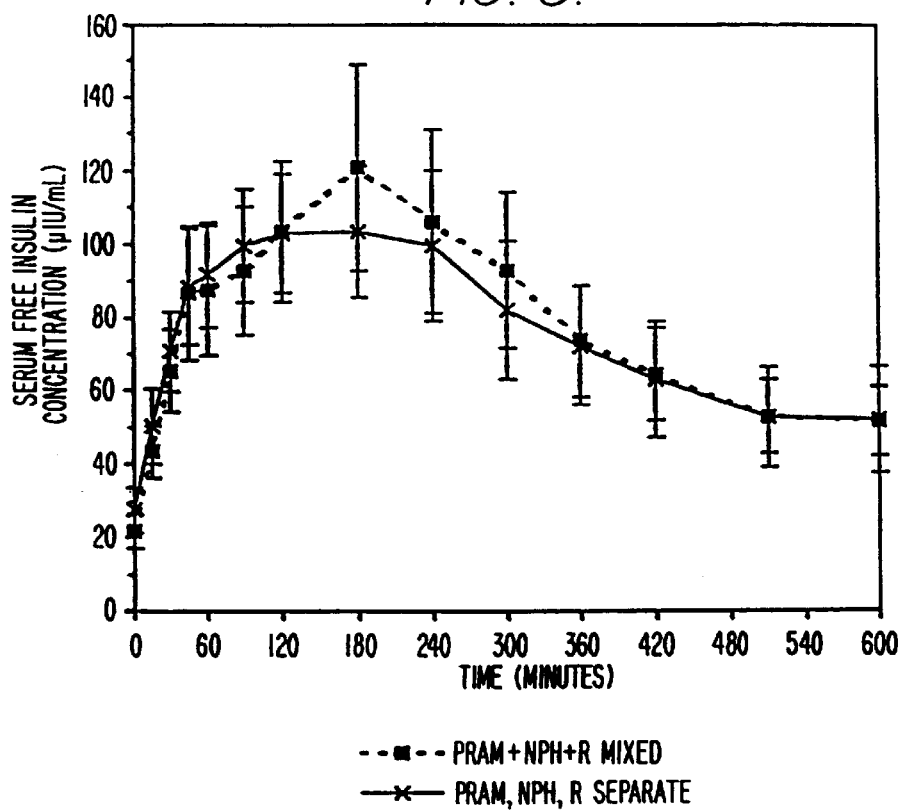
FIG. 8 shows serum free insulin concentrations after subcutaneous administration of pramlintide combined with NPH and regular insulin (PRAM+NPH+R mixed) compared to administration of pramlintide, NPH insulin, and regular insulin in separate injections in patients with Type I diabetes mellitus (Mean±SEM; N=30)

Mean serum free insulin concentrations following PRAM+NPH+R mixed compared to PRAM, NPH, R separate are displayed in FIG. 8. Mean serum free insulin concentrations following administration of PRAM+NPH+R mixed increased rapidly during the initial 45 minutes similar to PRAM, NPH, R separate. However, the mean serum free insulin concentrations from PRAM+NPH+R mixed continued to increase at a slower rate, but still more rapidly than for PRAM, NPH, R separate, to reach a higher mean peak concentration at approximately 180 minutes. After an initial rapid decrease between 180 and 240 minutes for PRAM+NPH+R mixed, mean serum free insulin concentrations declined at a similar rate for the two treatments throughout the remainder of the 600-minute sampling period. At 600 minutes, the mean serum free insulin concentration remained above the mean baseline serum free insulin concentration but was similar to that observed with pramlintide, NPH, R separate.

Figure 9:
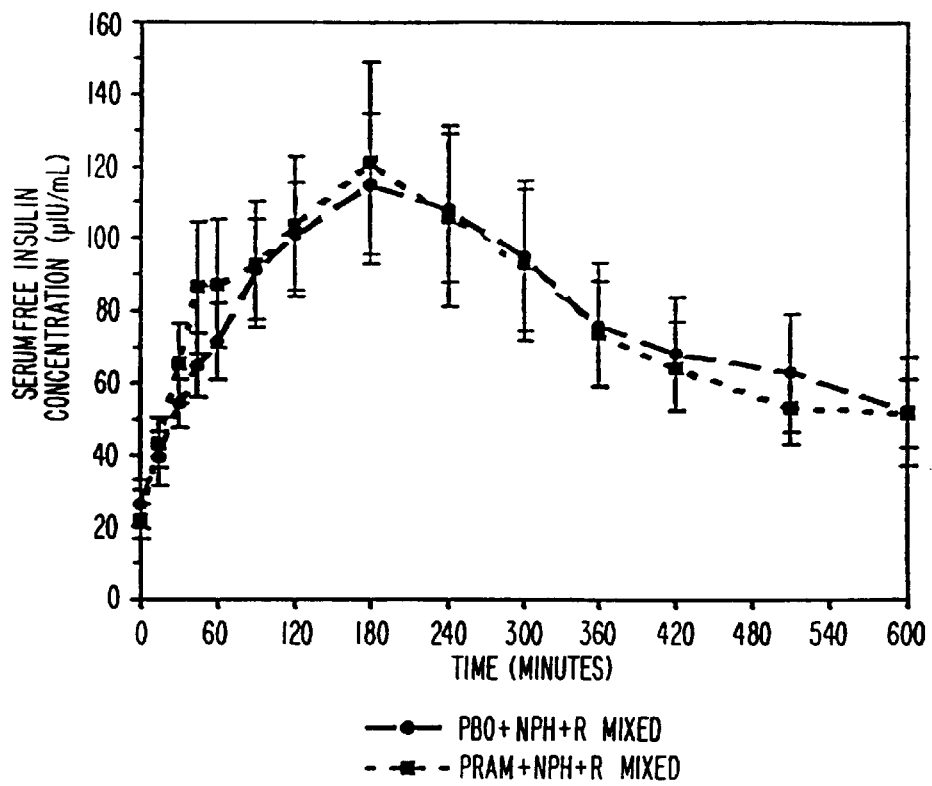
FIG. 9 shows serum free insulin concentrations after subcutaneous administration of pramlintide combined with NPH and regular insulin (PRAM+NPH+R mixed) compared to administration of placebo combined with NPH and regular insulin (PBO+NPH+R mixed) in patients with Type I diabetes mellitus (Mean±SEM; N=30).
Figure 10:
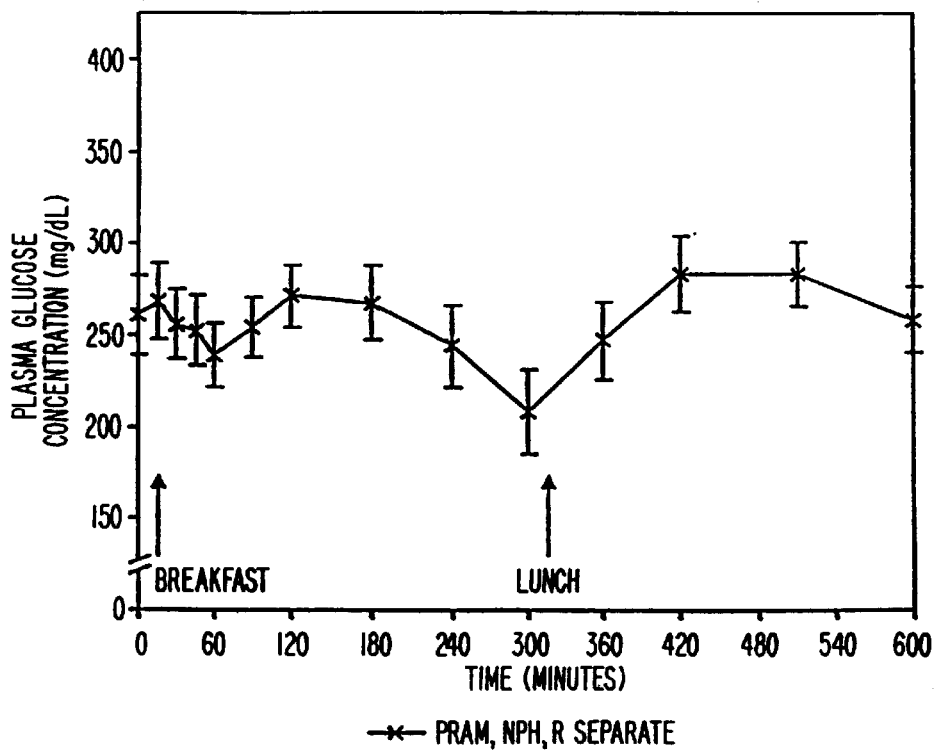
FIG. 10 shows plasma glucose concentrations after subcutaneous administration of pramlintide, NPH insulin, and regular insulin in separate injections in patients with Type I diabetes mellitus (Mean±SEM; N=30).

Mean serum free insulin concentrations following PRAM+NPH+R mixed compared to PBO+NPH+R mixed are displayed in FIG. 9. Mean serum free insulin concentrations following administration of PRAM+NPH+R mixed increased slightly more rapidly during the initial 45 minutes following injection than those after PBO+NPH+R mixed. Thereafter, mean serum free insulin concentrations from both treatments increased at a similar rate until reaching peak concentrations at 180 minutes. Following the peak, mean serum free insulin concentrations declined gradually throughout the remainder of the 600-minute sampling period for both treatments. At 600 minutes, mean serum free insulin concentrations remained above the mean baseline serum free insulin concentrations.

Mean±SEM serum free insulin pharmacokinetic parameter values for all evaluable patients for all treatments are displayed in Table 2.

TABLE 2

Free Insulin Pharmacokinetic Parameter Values in Patients with Type I Diabetes Mellitus Following Single Doses of Pramlintide, Regular Insulin, and NPH Insulin Administered as Separate and Combined Subcutaneous Injections [Mean ± SEM, Median, and Range; N = 30]

| Treatment/ Statistics | $AUC_{(0-600)}$ (: IUCmin/mL) | $C_{max}$ (: IU/mL) | $T_{max}$ (min) |
|---|---|---|---|
| PRAM, NPH, R separate[a] | | | |
| Mean ± SEM | 46076.8 ± 9303.3 | 121.4 ± 21.2 | 144.0 ± 15.3 |
| Median | 30255.60 | 76.7 | 120 |
| Min–Max | 17366.9–289368.6 | 44.6–645.4 | 0–360 |
| PRAM + R mixed, NPH separate[b] | | | |
| Mean ± SEM | 42654.0 ± 5792.2 | 132.7 ± 15.1 | 144.3 ± 13.5 |
| Median | 35279.25 | 114.3 | 151 |
| Min–Max | 13387.7–180646.1 | 38.8–400.6 | 0–241 |
| PRAM + NPH mixed, R separate[c] | | | |
| Mean ± SEM | 48193.0 ± 7790.4 | 126.9 ± 18.2 | 158.1 ± 11.0 |
| Median | 37520.90 | 111.9 | 180 |
| Min–Max | 17064.6–239463.0 | 48.2–563.4 | 45–242 |
| PRAM + NPH + R mixed[d] | | | |
| Mean ± SEM | 47775.1 ± 9343.9 | 146.6 ± 30.0 | 214.2 ± 24.0 |
| Median | 33897.85 | 100.1 | 180 |
| Min–Max | 12799.5–298288.2 | 36.0–882.4 | 30–603 |
| PBO + NPH + R mixed[e] | | | |
| Mean ± SEM | 47794.4 ± 9398.7 | 123.5 ± 20.5 | 194.2 ± 10.9 |
| Median | 33418.25 | 95.3 | 180 |
| Min–Max | 14018.9–300532.5 | 39.6–654.2 | 90–300 |

[a]Pramlintide, NPH insulin, and regular insulin in separate syringes.
[b]Pramlintide + regular insulin in one syringe, with NPH insulin separate.
[c]Pramlintide + NPH insulin in one syringe, with regular insulin separate.
[d]Pramlintide + NPH insulin + regular insulin in one syringe.
[e]Placebo (matching pramlintide) + NPH insulin + regular insulin in one syringe.

There was an increase in median serum free insulin $C_{max}$ (7% to 20%) associated with mixing pramlintide and regular and/or NPH insulin (PRAM+R mixed, NPH separate; PRAM+NPH mixed, R separate; and PRAM+NPH+R mixed) compared to PRAM, NPH, R separate. The increase in median insulin $C_{max}$ was greatest for PRAM+NPH mixed, R separate. There was a delay in median insulin $T_{max}$ associated with PRAM+NPH+R mixed compared to PRAM, NPH, R separate. There were delays in mean insulin $T_{max}$ associated with all treatments in which pramlintide was mixed with regular and/or NPH insulin compared to separate injections.

Following administration of PRAM+NPH mixed, R separate, insulin had slightly increased bioavailability compared to other treatments. However, this difference in mean profiles may be clinically indistinguishable, particularly when the high variability in the serum free insulin concentration data is considered. The conclusions for serum free insulin are as follows. (1) There was an increase in median insulin $C_{max}$ associated with mixing pramlintide with regular and/or NPH insulin compared to administration in separate injections. The increase in median $C_{max}$ was greatest when pramlintide was mixed with NPH insulin. There was a delay in median insulin $T_{max}$ when pramlintide, regular insulin, and NPH insulin all were mixed in the same syringe prior to injection. (2) When pramlintide was mixed with NPH insulin in one syringe and regular insulin was administered by separate injection, insulin appeared to have increased bioavailability based on the serum free insulin profile compared to other treatments between 0 and 300 minutes. (3) The insulin profiles following administration of pramlintide, regular insulin, and NPH insulin in a single injection were similar to those following administration of placebo, regular insulin, and NPH insulin in a single injection. (4) A slight increase in insulin $C_{max}$ was observed following administration of the pramlintide combined injection relative to the placebo combined injection; however, 90% confidence intervals demonstrated equivalence in all parameters between treatments.

Plasma Glucose Concentrations—Mean plasma glucose concentration-time profiles for all evaluable patients after all treatments are displayed in FIGS. 10–14. Mean plasma glucose concentrations following administration of PRAM, NPH, R separate are displayed in FIG. 10. Mean plasma glucose concentrations after PRAM, NPH, R separate fluctuated between approximately 210 and 285 mg/dL. Mean plasma glucose concentrations declined from 15 minutes (the time breakfast was provided) to 60 minutes after dosing, after which there was an increase from 60 to 120 minutes, followed by another decline to 300 minutes. From 300 to 420 minutes after dosing, with lunch ingested at 315 minutes, mean plasma glucose concentrations increased. Beginning at 510 minutes, mean plasma glucose concentrations decreased to approximately 260 mg/dL at 600 minutes.

Figure 11:
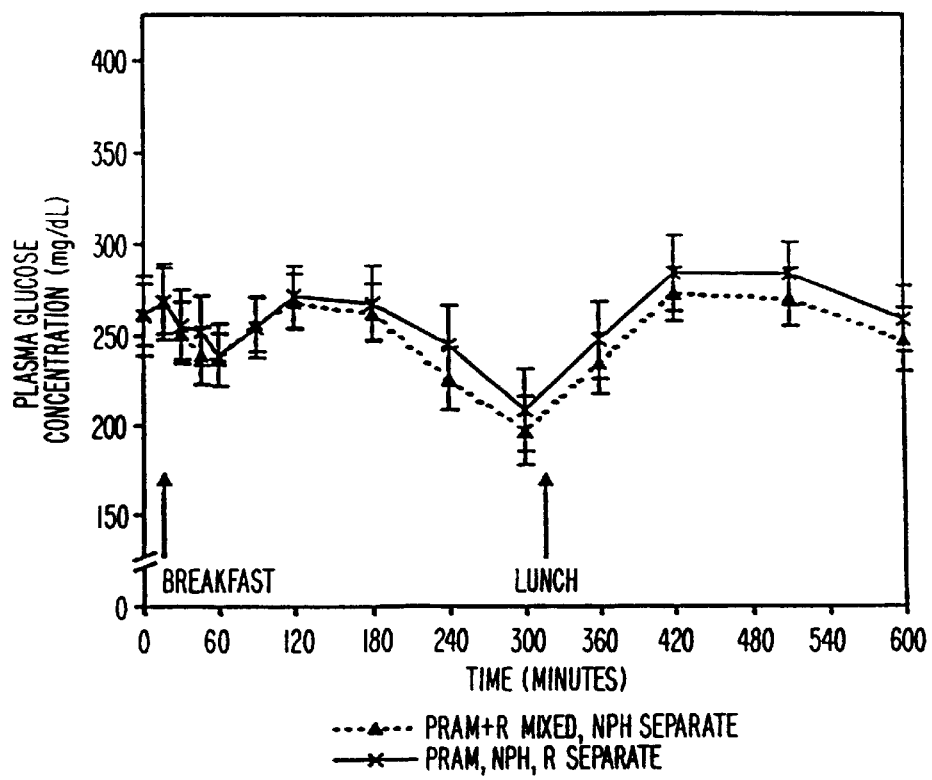
FIG. 11 shows plasma glucose concentrations after subcutaneous administration of pramlintide combined with regular insulin (PRAM+R mixed, NPH separate) compared to administration of pramlintide, NPH insulin, and regular insulin in separate injections in patients with Type I diabetes mellitus (Mean±SEM; N=30).

Mean plasma glucose concentrations following PRAM+R mixed, NPH separate compared to PRAM, NPH, R separate are displayed in FIG. 11. The mean plasma glucose concentration profile following administration of PRAM+R mixed, NPH separate was similar in shape to that for PRAM, NPH, R separate and mean concentrations fluctuated between approximately 200 and 275 mg/dL. The two profiles were almost superimposable for the first 120 minutes following administration. From 180 to 600 minutes after dosing, mean plasma glucose concentrations for PRAM+R mixed, NPH separate were slightly elevated but followed the same time course as the profile for PRAM, NPH, R separate and declined to approximately 250 mg/dL at 600 minutes.

Figure 12:
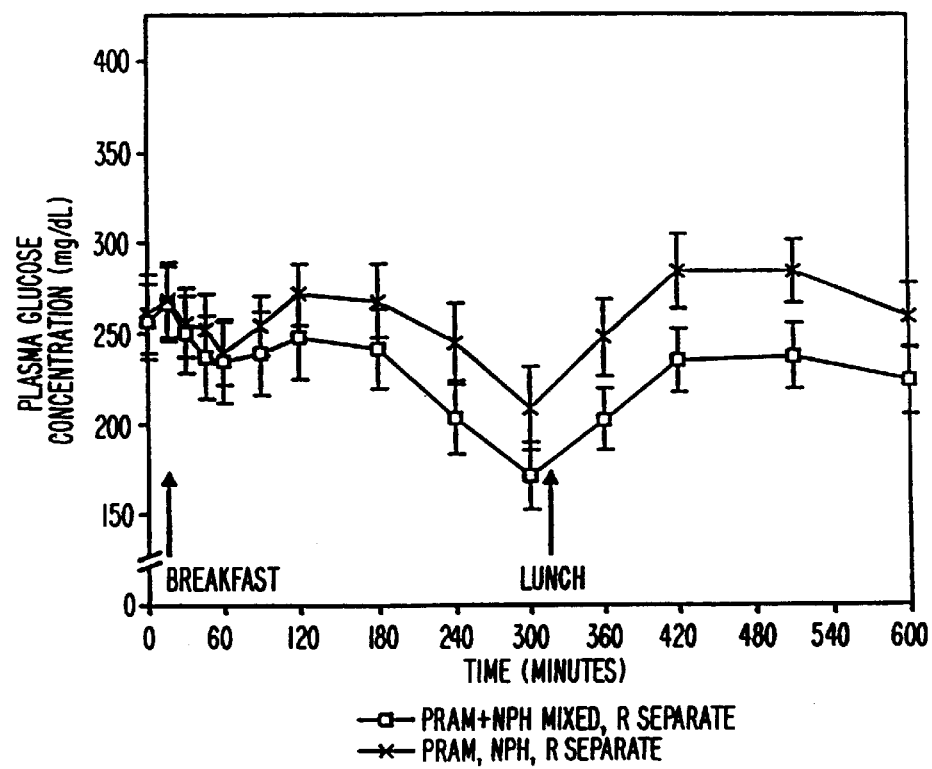
FIG. 12 shows plasma glucose concentrations after subcutaneous administration of pramlintide combined with NPH insulin (PRAM+NPH mixed, r separate) compared to administration of pramlintide, NPH insulin, and regular insulin in separate injections in patients with Type I diabetes mellitus (Mean±SEM; N=30).
Figure 15:
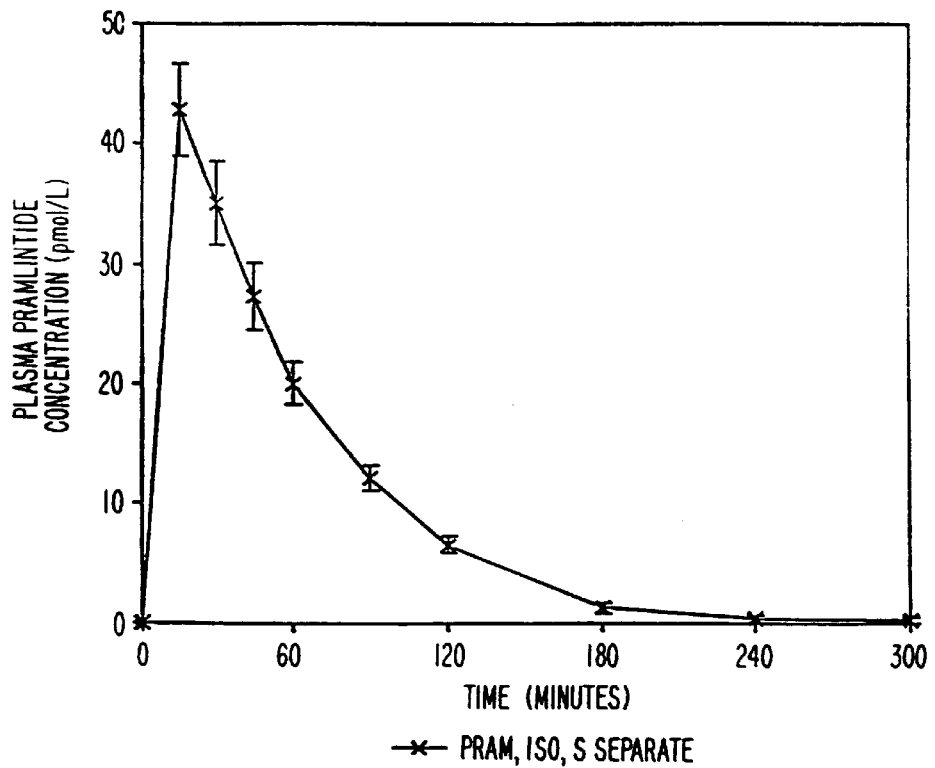
FIG. 15 shows plasma pramlintide concentrations after subcutaneous administration of pramlintide, isophane insulin, and soluble insulin in separate injections in patients with Type I diabetes mellitus (Mean±SEM; N=26).

Mean plasma glucose concentrations following administration of PRAM+NPH mixed, R separate compared to PRAM, NPH, R separate are displayed in FIG. 12. The mean plasma glucose concentration profile following administration of PRAM+NPH mixed, R separate was similar in shape to that for PRAM, NPH, R separate and fluctuated between approximately 170 and 265 mg/dL. The two profiles were almost superimposable for the first 60 minutes following administration. From 60 to 600 minutes after dosing, mean plasma glucose concentrations for PRAM+NPH mixed, R separate were lower but followed the same time course as those after administration of PRAM, NPH, R separate and had reached approximately 225 mg/dL at 600 minutes.

Mean plasma glucose concentrations following administration of PRAM+NPH+R mixed compared to PRAM, NPH, R separate are displayed in FIG. 13. The mean plasma glucose concentration profile following administration of PRAM+NPH+R mixed was similar in shape to that after PRAM, NPH, R separate and mean concentrations fluctuated between approximately 185 and 270 mg/dL. The two profiles were almost superimposable for the first 120 minutes following administration. From 120 to 600 minutes after dosing, mean plasma glucose concentrations for PRAM+NPH+R mixed were lower but followed the same time course as those after administration of PRAM, NPH, R separate and declined to approximately 205 mg/dL at 600 minutes.

Mean plasma glucose concentrations following administration of PBO+NPH+R mixed compared to PRAM+NPH+R mixed are displayed in FIG. 14. Mean plasma glucose concentrations were higher after breakfast for up to 240 minutes after administration of PBO+NPH+R mixed compared to PRAM+NPH+R mixed. This is consistent with the effect of pramlintide to lower plasma glucose concentrations following meal ingestion within the first 180 to 240 minutes after dosing. After 300 minutes, the mean plasma glucose concentration profile from PBO+NPH+R mixed was similar to that for PRAM+NPH+R mixed. Mean plasma glucose concentrations were approximately 220 mg/dL at 600 minutes after PBO+NPH+R mixed compared to approximately 205 mg/dL after PRAM+NPH+R mixed.

Mean±SEM plasma glucose $AUC_{(0-600)}$, $C_{max}$, and $T_{max}$ values for all evaluable patients after all treatments are displayed in Table 3.

TABLE 3

Plasma Glucose Parameter Values in Patients with Type I Diabetes Mellitus Following Single Doses of Pramlintide, Regular Insulin, and NPH Insulin Administered as Separate and Combined Subcutaneous Injections [Mean ± SEM, Median, and Range; N = 30]

| Treatment/ Statistics | $AUC_{(0-600)}$ (mgCmin/dL) | $C_{max}$ (mg/dL) | $T_{max}$ (min) |
|---|---|---|---|
| PRAM, NPH, R separate[a] | | | |
| Mean ± SEM | 154585.8 ± 9587.5 | 369.2 ± 15.0 | 263.7 ± 39.9 |
| Median | 158802.0 | 368.5 | 240.5 |
| Min–Max | 64815–282499 | 254–595 | 0–601 |
| PRAM + R mixed, NPH separate[b] | | | |
| Mean ± SEM | 149775.6 ± 7075.1 | 348.9 ± 10.6 | 251.7 ± 40.5 |
| Median | 145347.0 | 347.0 | 180.0 |
| Min–Max | 69143–221104 | 235–475 | 0–600 |
| PRAM + NPH mixed, R separate[c] | | | |
| Mean ± SEM | 134735.6 ± 9884.1 | 324.1 ± 18.0 | 224.7 ± 40.3 |
| Median | 118852.5 | 321.5 | 150.5 |
| Min–Max | 47635–225321 | 131–518 | 0–600 |
| PRAM + NPH + Rmixed[d] | | | |
| Mean ± SEM | 136311.0 ± 8983.7 | 328.4 ± 15.5 | 140.6 ± 25.3 |
| Median | 132862.0 | 346.0 | 120.0 |
| Min–Max | 44738–221578 | 151–473 | –510 |
| PBO + NPH + R mixed[e] | | | |
| Mean ± SEM | 150688.0 ± 7957.8 | 390.5 ± 18.3 | 194.2 ± 33.1 |
| Median | 149629.3 | 397.0 | 120.0 |
| Min–Max | 64499–236393 | 156–637 | 15–600 |

[a]Pramlintide, NPH insulin, and regular insulin in separate syringes.
[b]Pramlintide + regular insulin in one syringe, with NPH insulin separate.
[c]Pramlintide + NPH insulin in one syringe, with regular insulin separate.
[d]Pramlintide + NPH insulin + regular insulin in one syringe.
[e]Placebo (matching pramlintide) + NPH insulin + regular insulin in one syringe.

Mean baseline plasma glucose concentrations were approximately 250 to 260 mg/dL for all treatments.

There was a decrease in median plasma glucose $C_{max}$ (11% to 13%) associated with mixing pramlintide and NPH insulin (PRAM+NPH mixed, R separate and PRAM+NPH+R mixed) compared to PRAM, NPH, R separate. Although mean ratios indicated a delay in plasma glucose $T_{max}$ for PRAM+R mixed, NPH separate; PRAM+NPH mixed, R separate; and PRAM+NPH+R mixed compared to PRAM, NPH, R separate, median ratios indicated $T_{max}$ was shorter when pramlintide, regular insulin, and NPH insulin were mixed.

Administration of PRAM+R mixed, NPH separate resulted in comparable plasma glucose $AUC_{(0-600)}$ values to that following PRAM, NPH, R separate; however, decreases in median $AUC_{(0-600)}$ values were observed when pramlintide was mixed with NPH insulin with and without regular insulin.

Significant deviations from normality were not observed for the loge-transformed values for the variables $C_{max}$ and $AUC_{(0-600)}$ for plasma glucose. There was no period effect observed during statistical analysis of the data.

The conclusions for plasma glucose are as follows. (1) There was a decrease in median glucose $C_{max}$ values associated with mixing pramlintide with NPH insulin compared to administration in separate injections. (2) Although mean ratios indicate a delay in $T_{max}$ when pramlintide was mixed with regular and/or NPH insulin, median $T_{max}$ values were either comparable (PRAM+R mixed, NPH separate and PRAM+NPH mixed, R separate) or shorter (PRAM+NPH+R mixed) compared to separate injections. (3) After lunch, a lower glucose peak was observed for both treatments when pramlintide and NPH insulin were mixed prior to injection than when NPH insulin was administered in a separate injection. (4) Median glucose $C_{max}$ values were lower (16%). Between treatment comparisons for glucose $C_{max}$ were statistically significant (p=0.0010); however, $T_{max}$ values were not significantly different after administration of pramlintide, regular insulin, and NPH insulin combined in a single injection relative to placebo, regular insulin, and NPH insulin combined in a single injection. (5) Up to 300 minutes after dosing, administration of the four pramlintide treatments resulted in lower glucose profiles compared to that after administration of the placebo treatment. After 300 minutes, the glucose profiles were similar for the placebo treatment, pramlintide combined with both NPH and regular insulin, and pramlintide combined with NPH insulin in one injection. (6) Over the entire time period (0 to 600 minutes) the glucose profile was clinically optimal with the combination of pramlintide and NPH insulin in one syringe with or without regular insulin compared to the other treatments.

The study results demonstrate that there is no disadvantage in mixing pramlintide with regular insulin and/or NPH insulin prior to injection. Furthermore, and importantly, the results demonstrate that there is an advantage, with respect to glucose control, to mixing pramlintide and NPH insulin prior to injection.

EXAMPLE 2

In this study, patients with Type I diabetes mellitus who were using soluble insulin and isophane insulin were enrolled and randomized to receive each of the following five treatments administered subcutaneously in random sequence with 1-week washout periods between treatments: (1) pramlintide in one syringe, isophane insulin in another syringe, and soluble insulin in a third syringe [PRAM, ISO, S separate]; (2) pramlintide and soluble insulin in one syringe and a separate injection of isophane insulin [PRAM+S mixed, ISO separate]; (3) pramlintide and isophane insulin in one syringe and a separate injection of soluble insulin [PRAM+ISO mixed, S separate]; (4) pramlintide, isophane insulin, and soluble insulin in a single injection [PRAM+ISO+S mixed]; and (5) placebo (matching pramlintide), isophane insulin, and soluble insulin in a single injection [PBO+ISO+S mixed].

Set forth below are the pharmacokinetic results for plasma pramlintide for the four treatments containing pramlintide and the pharmacokinetic results for serum free insulin for all five treatments. The effects of pramlintide and insulin administration on plasma glucose (glucose pharmacodynamics) for all five treatments are also presented. The pharmacodynamic effect of administering pramlintide mixed with soluble and/or isophane insulin on the plasma glucose profile was assessed and is expressed using pharmacokinetic parameters. The plasma glucose profiles during the breakfast and lunch periods are described.

This trial was designed as an open-label, single-center, five-period, randomised, crossover study with 1-week washout periods between treatments to compare profiles for plasma pramlintide, serum free insulin, and plasma glucose after pramlintide, isophane (Novo Nordisk) human insulin, and soluble (Novo Nordisk) human insulin were mixed and administered together and as separate subcutaneous injections.

Treatments were administered in randomized sequence at approximately 7:00 AM (Time 0), 15 minutes prior to breakfast on study days separated by a one week washout period. (Time 0 minutes on all figures represents the time of study drug administration.) On dosing days, patients received one of five treatments containing pramlintide or placebo and isophane or soluble insulin administered combined or as separate injections in randomized sequence. The pramlintide dose was 30 µg in all treatments containing pramlintide. Throughout the study period, patients maintained a stable diet and continued to receive their usual soluble and isophane insulin doses. All treatments were administered by subcutaneous injection into the anterior abdominal wall. All syringes were given to the patient for self-administration within 5 minutes of preparation.

Blood samples for plasma pramlintide, serum free insulin, and plasma glucose concentrations were obtained at the following time points: 0 (predose), 15, 30, 45, 60, 90, 120, 180 minutes (3 hours), 4, and 5 hours following administration of study drug on study days 2, 4, 6, 8, and 10. In addition, blood samples were collected at 6, 7, 8.5, and 10 hours after dosing on the same days for serum free insulin and plasma glucose concentrations.

On each dosing day, identical meals (breakfast and lunch) were eaten. Patients ate their standardized lunch at 12:15 PM, 15 minutes after collection of the 5-hour blood samples. There was no noontime administration of any study drug, including insulin.

The following pharmacokinetic parameters were calculated from the plasma pramlintide, serum free insulin and plasma glucose concentrations: $C_{max}$ (the peak concentration determined as the highest observed concentration during the blood sampling interval); $T_{max}$ (the blood sampling time at which $C_{max}$ occurred); and, $AUC_{(0-t)}$ (the area under the concentration-time profile determined using the trapezoidal rule, where t=300 minutes (5 hours) for plasma pramlintide and t=600 minutes (10 hours) for serum free insulin and plasma glucose). Glucose parameters were also calculated for the meal periods. In addition, the mean concentration-time profiles for plasma pramlintide, serum free insulin, and plasma glucose following each treatment were calculated. Since $T_{max}$ varies between patients, the peak concentrations contained in the mean profiles do not correspond to median or mean $C_{max}$ values.

The effect of meals on plasma glucose profiles was evaluated by calculating AUC, $C_{max}$ and $T_{max}$ values for the periods that included breakfast (0 to 300 minutes) and the period that included lunch (300 to 600 minutes). Statistical analysis of the variables $AUC_{(0-300)}$, $C_{max}$, and $T_{max}$ for glucose during the breakfast period and $AUC_{(300-600)}$, $C_{max}$, and $T_{max}$ for glucose during the lunch period was as described for glucose.

Pharmacokinetics—Mean plasma pramlintide concentration-time profiles and pharmacokinetics are described and compared between treatments.

Plasma Pramlintide Concentrations—Mean plasma pramlintide concentration-time profiles for all evaluable patients after all pramlintide treatments, are displayed in FIGS. 15–18. Mean plasma pramlintide concentrations following administration of pramlintide, isophane insulin, and soluble insulin (PRAM, ISO, S separate) in separate syringes are displayed in FIG. 15. Following subcutaneous administration of pramlintide, soluble insulin, and isophane insulin in separate syringes, the plasma concentration profile indicates that mean plasma pramlintide concentrations increased rapidly, reached peak concentration at 15 minutes after dosing, and declined rapidly thereafter to approach baseline at approximately 300 minutes after dosing.

Figure 16:
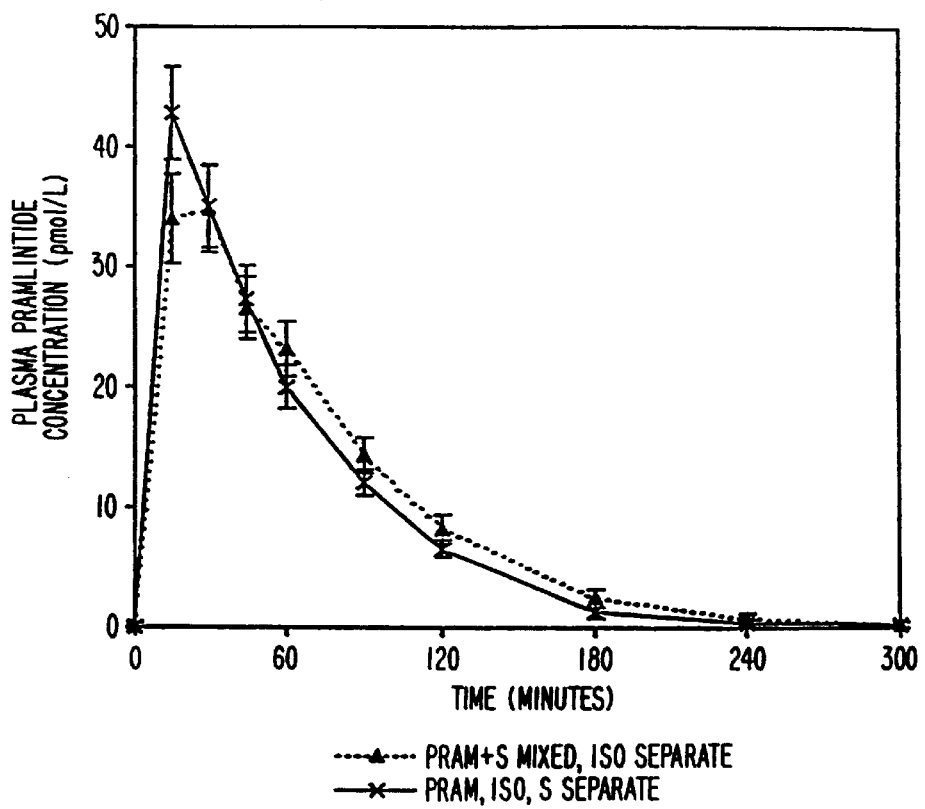
FIG. 16 shows plasma pramlintide concentrations after subcutaneous administration of pramlintide combined with soluble insulin (PRAM+S mixed, ISO separate) compared to administration of pramlintide, isophane insulin, and soluble insulin in separate injections in patients with Type I diabetes mellitus (Mean±SEM; N=26)

Mean plasma pramlintide concentrations following administration of PRAM+S mixed, ISO separate compared to administration of PRAM, ISO, S separate are displayed in FIG. 16. Following subcutaneous administration of PRAM+S mixed, ISO separate, mean plasma pramlintide concentrations increased with time, reached peak concentrations at approximately 30 minutes after the dose, and declined rapidly thereafter to baseline at 300 minutes. Although the plasma pramlintide concentration profile was similar compared to PRAM, ISO, S separate, the mean peak concentration was reached later and was not as high.

Figure 17:
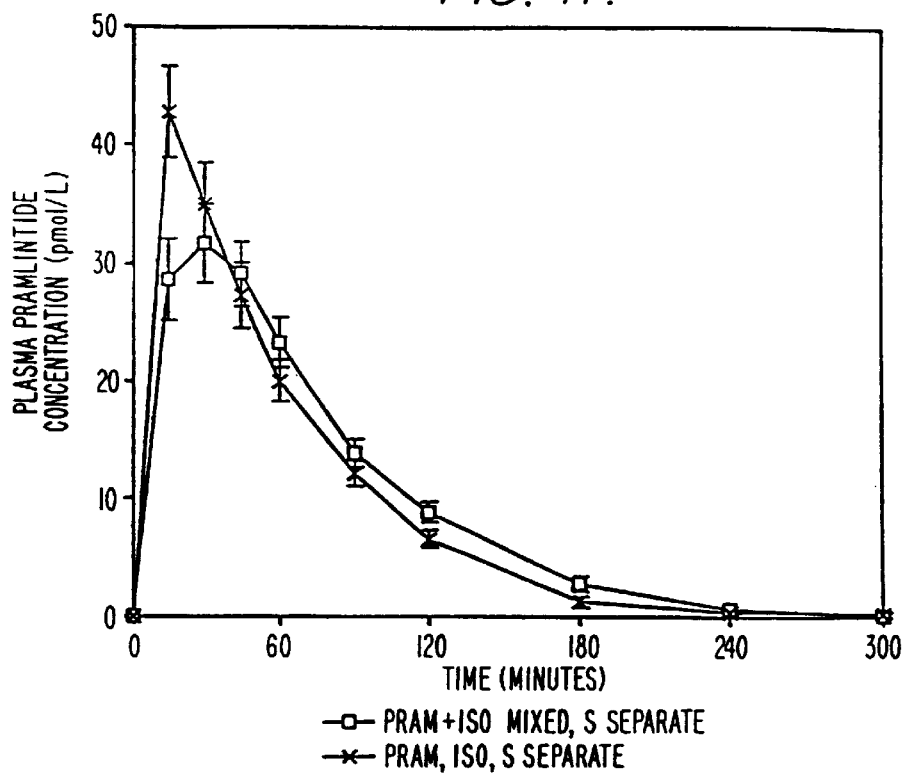
FIG. 17 shows plasma pramlintide concentrations after subcutaneous administration of pramlintide combined with isophane insulin (PRAM+ISO mixed, S separate) compared to administration of pramlintide, isophane insulin, and soluble insulin in separate injections in patients with Type I diabetes mellitus (Mean±SEM; N=26)

Mean plasma pramlintide concentrations following administration of PRAM+ISO mixed, S separate compared to PRAM, ISO, S separate are displayed in FIG. 17. Following subcutaneous administration of PRAM+ISO mixed, S separate, mean plasma pramlintide concentrations increased with time, reached peak concentrations at 30 minutes after the dose, and declined rapidly thereafter to baseline at 300 minutes. Compared to PRAM, ISO, S separate, the mean peak concentration was reached later and was not as high.

Figure 18:
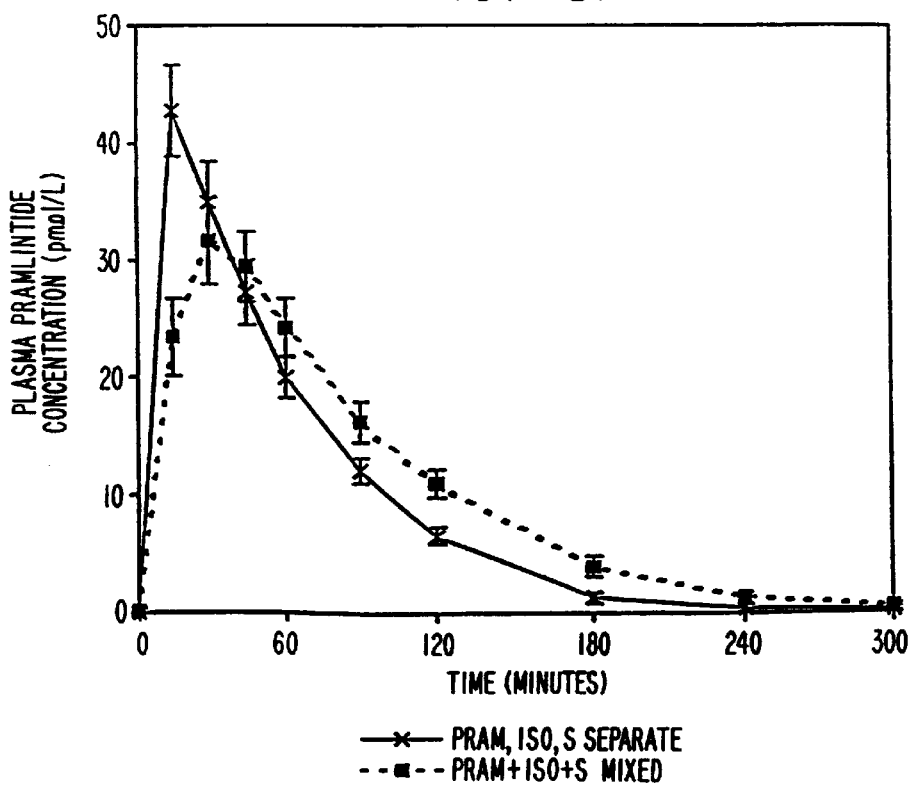
FIG. 18 shows plasma pramlintide concentrations after subcutaneous administration of pramlintide, combined with isophane insulin and soluble insulin (PRAM+ISO+S) compared to administration of pramlintide, isophane insulin, and soluble insulin in separate injections in patients with Type I diabetes mellitus (Mean±SEM; N=26)
Figure 19:
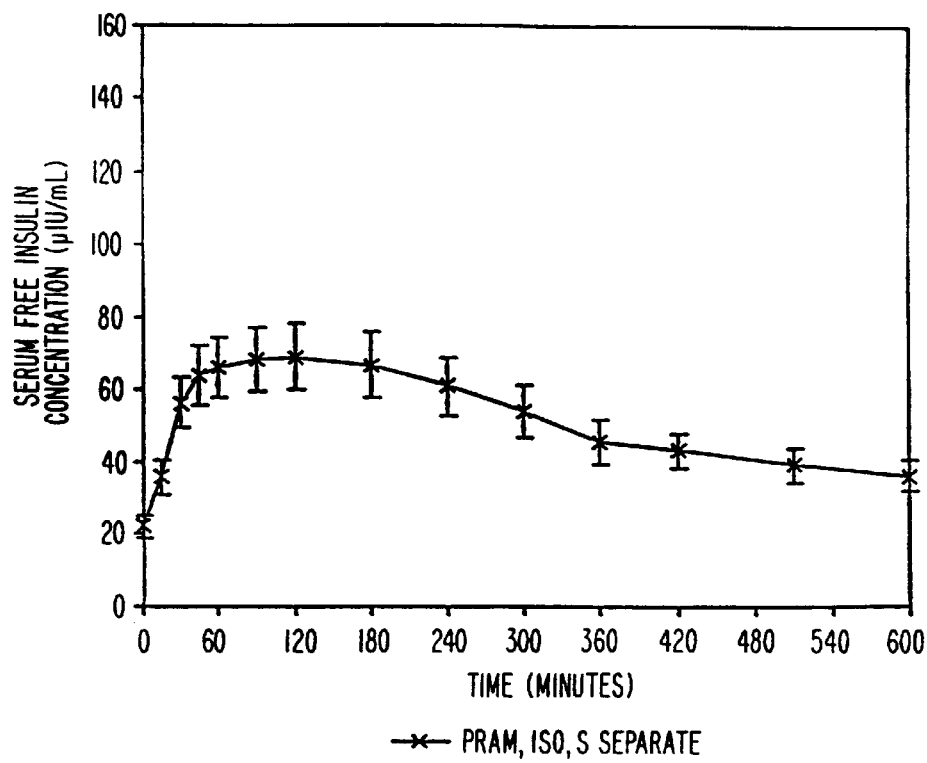
FIG. 19 shows serum free insulin concentrations after subcutaneous administration of pramlintide, isophane insulin, and soluble insulin in separate injections in patients with Type I diabetes mellitus (Mean±SEM; N=27).

Mean plasma pramlintide concentrations following administration of PRAM+ISO+S mixed compared to PRAM, ISO, S separate are displayed in FIG. 18. The mean plasma pramlintide concentrations after the administration of PRAM+ISO+S mixed increased with time, reached peak concentrations at 30 minutes after the dose, and declined rapidly thereafter to baseline at 300 minutes. Compared to PRAM, ISO, S separate, the mean peak concentration was reached later and was not as high, and the decline was not as rapid.

Plasma Pramlintide Pharmacokinetic Parameters—Mean±SEM plasma pramlintide pharmacokinetic parameter values for all evaluable patients following all pramlintide-containing treatments are displayed in Table 4.

TABLE 4

Plasma Pramlintide Pharmacokinetic Parameter Values in Patients with Type I Diabetes Mellitus Following Single Doses of Pramlintide, Soluble Insulin, and Isophane Insulin Administered as Separate and Combined Subcutaneous Injections [Mean ± SEM, Median, and Range; N = 26]

| Treatment/ Statistics | $AUC_{(0-300)}$ (pmolCmin/L) | $C_{max}$ (pmol/L) | $T_{max}$ (min) |
|---|---|---|---|
| PRAM, ISO, S separate[a] | | | |
| Mean ± SEM | 2797.8 ± 241.7 21.4 ± 3.3 | | 44.35 ± 3.65 |
| Median | 2863.5 | 41.39 | 15 |
| Min–Max | 1053.2–5721.6 | 14.14–85.42 | 5–90 |
| PRAM + S mixed, ISO separate[b] | | | |
| Mean ± SEM | 2954.6 ± 291.6 25.1 ± 2.5 | | 39.75 ± 3.43 |
| Median | 2641.7 | 34.02 | 22 |
| Min–Max | 1174.8–7257.2 | 12.00–84.72 | 10–60 |
| PRAM + ISO mixed, S separate[c] | | | |
| Mean ± SEM | 2894.1 ± 242.5 | 35.57 ± 3.48 | 31.6 ± 3.0 |
| Median | 2870.4 | 31.95 | 30 |
| Min–Max | 516.5–5848.6 | 13.08–76.13 | 10–60 |
| PRAM + ISO + S mixed[d] | | | |
| Mean ± SEM | 3121.7 ± 323.4 | 34.13 ± 3.65 | 32.8 ± 2.1 |
| Median | 3150.4 | 31.74 | 30 |
| Min–Max | 406.3–6084.2 | 8.88–69.45 | 15–45 |

[a]Pramlintide, isophane insulin, and soluble insulin in separate syringes.
[b]Pramlintide + soluble insulin in one syringe, with isophane insulin separate.
[c]Pramlintide + isophane insulin in one syringe with soluble insulin separate.
[d]Pramlintide + isophane insulin + soluble insulin in one syringe.

The results of this trial support a number of conclusions for plasma pramlintide. Pramlintide was rapidly absorbed and eliminated following administration of pramlintide, soluble insulin, and isophane insulin administered as separate and in various combined subcutaneous injections. When mixed with soluble and/or isophane insulin, pramlintide had equivalent bioavailability compared to separate injections as evidenced by values for $AUC_{(0-300)}$. Median $C_{max}$ values were lower when pramlintide was mixed with isophane insulin prior to administration. There was a delay in median pramlintide $T_{max}$ when pramlintide was mixed with isophane insulin with and without soluble insulin. There was also a delay in mean pramlintide $T_{max}$ but not in median $T_{max}$ when pramlintide and soluble insulin were combined and isophane insulin was separate.

Serum Free Insulin Concentrations—Mean serum free insulin concentration-time profiles for all evaluable patients after all treatments are displayed in FIGS. 19–23. Mean serum free insulin concentrations following administration of PRAM, ISO, S separate are displayed in FIG. 19. Mean serum free insulin concentrations increased rapidly during the initial 45 minutes following administration PRAM, ISO, S separate. Thereafter, mean serum free insulin concentrations continued to increase but at a slower rate until peak concentration was reached at approximately 120 minutes. After the peak, mean serum free insulin concentrations declined slowly over the remainder of the 600-minute sampling period. At 600 minutes, the mean free insulin concentration remained above the mean baseline serum free insulin concentration.

Figure 20:
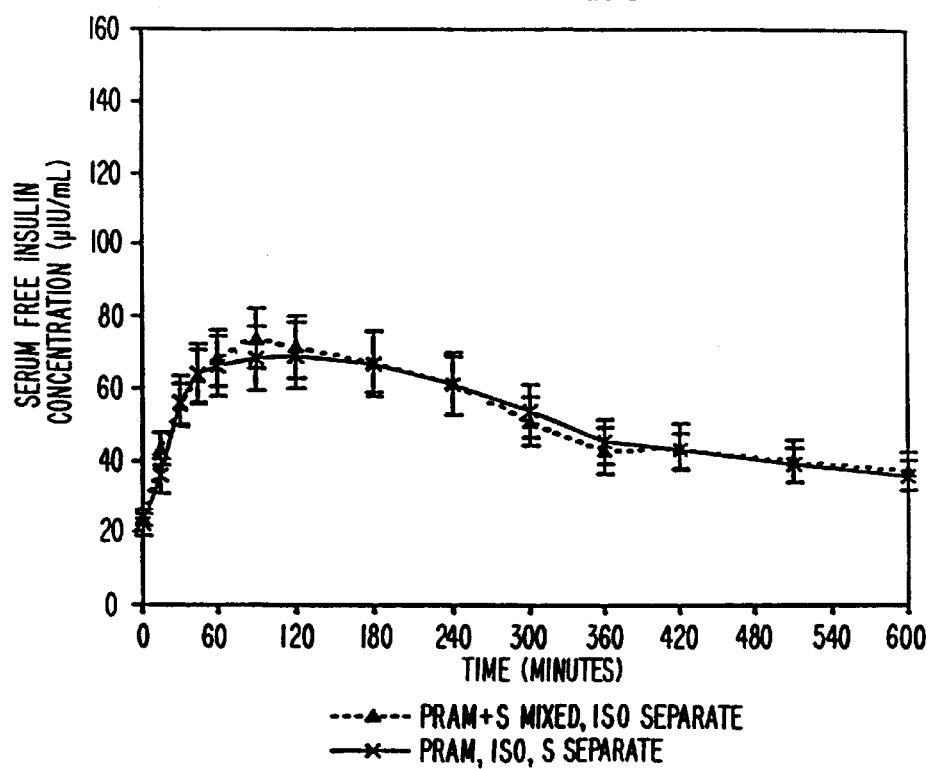
FIG. 20 shows serum free insulin concentrations after subcutaneous administration of pramlintide combined with soluble insulin (PRAM+S mixed, ISO separate) compared to administration of pramlintide, isophane insulin, and soluble insulin in separate injections in patients with Type I diabetes mellitus (Mean±SEM; N=27).

Mean serum free insulin concentrations following PRAM+S mixed, ISO separate compared to PRAM, ISO, S separate are displayed in FIG. 20. The mean serum free insulin concentration-time profile following administration of PRAM+S mixed, ISO separate was similar to that for administration of PRAM, ISO, S separate. For both treatments, mean serum free insulin concentrations increased rapidly during the initial 45 minutes following administration and continued to increase but at a slower rate until peak concentrations were reached between 90 and 120 minutes after dosing. After the peak, mean serum free insulin concentrations declined slowly over the remainder of the 600-minute sampling period. At 600 minutes, mean serum free insulin concentrations remained above the mean baseline serum free insulin concentrations.

Figure 21:
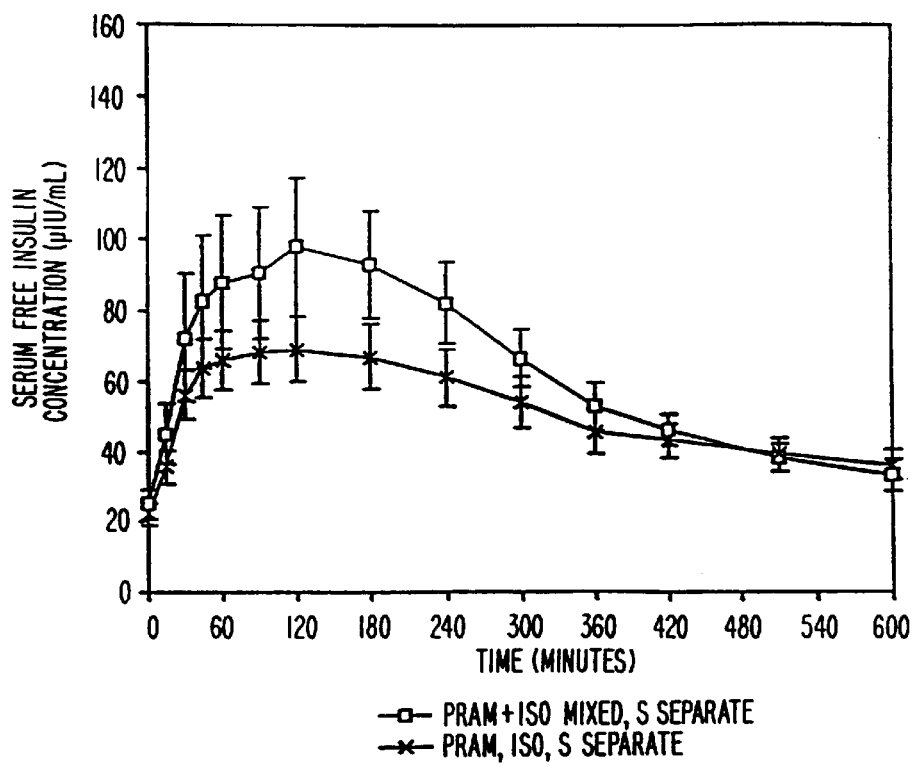
FIG. 21 shows serum free insulin concentrations after subcutaneous administration of pramlintide combined with isophane insulin (PRAM+ISO mixed, S separate) compared to administration of pramlintide, isophane insulin, and soluble insulin in separate injections in patients with Type I diabetes mellitus (Mean±SEM; N=27)

Mean serum free insulin concentrations following PRAM+ISO mixed, S separate compared to PRAM, ISO, S separate are displayed in FIG. 21. Mean serum free insulin concentrations were higher throughout most of the profile following administration of PRAM+ISO mixed, S separate compared to the mean concentrations for PRAM, ISO, S separate. Mean serum free insulin concentrations increased more rapidly for PRAM+ISO mixed, S separate to reach a higher mean peak concentration at approximately 120 minutes compared to that reached at the same time for PRAM, ISO, S separate. Following the peak, mean serum free insulin concentrations remained higher than those for PRAM, ISO, S separate up to 420 minutes after dosing. Thereafter, concentrations declined at a similar rate. At 600 minutes, the mean serum free insulin concentration remained above the mean baseline serum free insulin concentration but was similar to that observed with PRAM, ISO, S separate.

Figure 22:
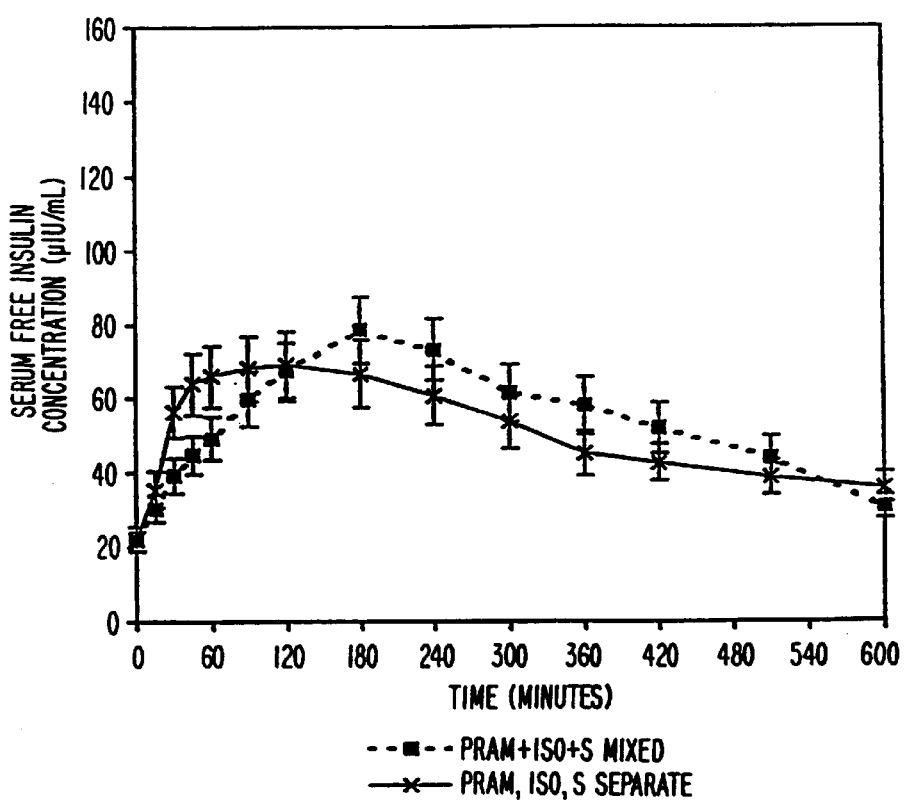
FIG. 22 shows serum free insulin concentrations after subcutaneous administration of pramlintide combined with isophane insulin and soluble insulin (PRAM+ISO+S mixed) compared to administration of pramlintide, isophane insulin, and soluble insulin in separate injections in patients with Type I diabetes mellitus (Mean±SEM; N=27)

Mean serum free insulin concentrations following PRAM+ISO+S mixed compared to PRAM, ISO, S separate are displayed in FIG. 22. Mean serum free insulin concentrations following administration of PRAM+ISO+S mixed increased more slowly during the initial 45 minutes compared to PRAM, ISO, S separate. The mean serum free insulin concentrations for PRAM+ISO+S mixed continued to increase to reach a higher peak than for PRAM, ISO, S separate at approximately 180 minutes. Mean serum free insulin concentrations declined slowly at a similar rate for the two treatments throughout the remainder of the 600-minute sampling period. At 600 minutes, the mean serum free insulin concentration for PRAM+ISO+S mixed remained above the mean baseline serum free insulin concentration and similar to that observed with PRAM, ISO, S separate.

Figure 23:
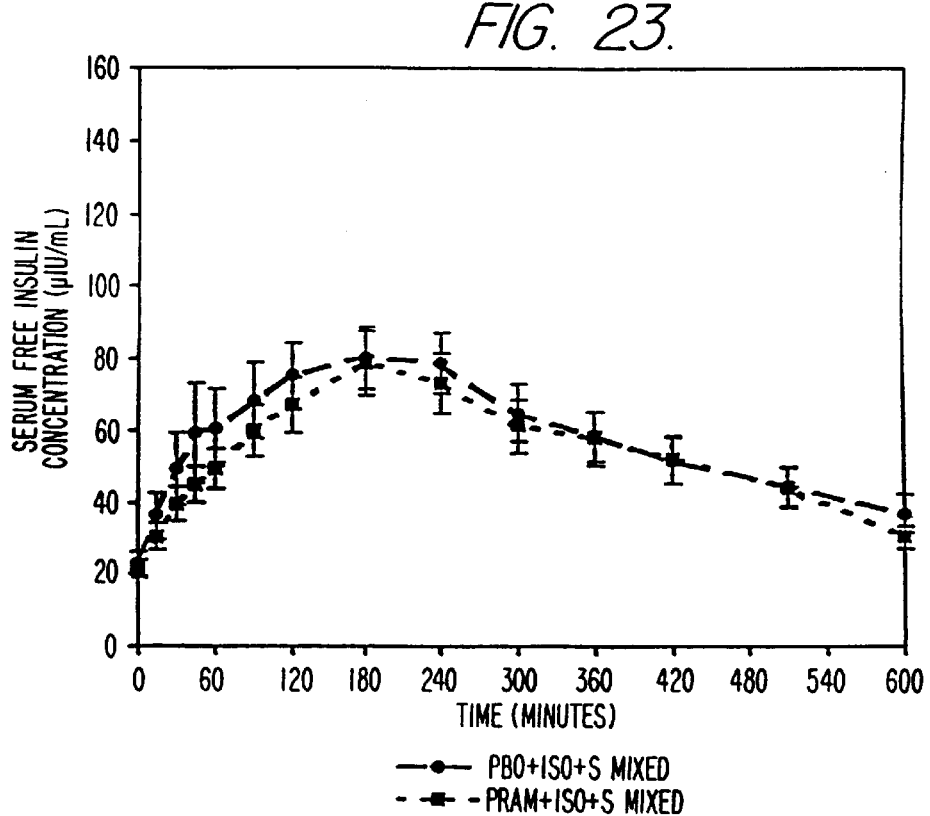
FIG. 23 shows serum free insulin concentrations after subcutaneous administration of pramlintide combined with isophane insulin and soluble insulin (PRAM+ISO+S mixed) compared to administration of placebo combined with isophane insulin and soluble insulin (PBO+ISO+S mixed) in patients with Type I diabetes mellitus (Mean±SEM; N=27)

Mean serum free insulin concentrations following PRAM+ISO+S mixed compared to PBO+ISO+S mixed are displayed in FIG. 23. Mean serum free insulin concentrations following administration of PRAM+ISO+S mixed increased slightly more rapidly during the initial 45 minutes following injection than those after PBO+ISO+S mixed. Thereafter, mean serum free insulin concentrations for both treatments increased at a similar rate until reaching peak concentrations at 180 minutes. Following the peak, mean serum free insulin concentrations declined gradually throughout the remainder of the 600-minute sampling period for both treatments. At 600 minutes, mean serum free insulin concentrations remained above the mean baseline serum free insulin concentrations.

Serum Free Insulin Pharmacokinetic Parameters—
Mean±SEM serum free insulin pharmacokinetic parameter values for all evaluable patients for all treatments are displayed in Table 5.

TABLE 5

Serum Free Insulin Pharmacokinetic Parameter Values in Patients with Type I Diabetes Mellitus Following Single Doses of Pramlintide, Soluble Insulin, and Isophane Insulin Administered as Separate and Combined Subcutaneous Injections [Mean ± SEM, Median, and Range; N = 27]

| Treatment/ Statistics ($\mu$IU/mL) | AUC$_{(0-600)}$ (min) | C$_{max}$ ($\mu$IUCmin/mL) | T$_{max}$ |
|---|---|---|---|
| PRAM, ISO, S separate[a] | | | |
| Mean ± SEM | 30898.1 ± 3749.4 | 83.8 ± 9.0 | 146.1 ± 18.9 |
| Median | 26734.5 | 70.2 | 120 |
| Minimum-Maximum | 10300.0–103011.0 | 24.4–240.6 | 30–420 |
| PRAM + S mixed, ISO separate[b] | | | |
| Mean ± SEM | 31067.7 ± 3983.6 | 81.0 ± 8.6 | 116.6 ± 12.5 |
| Median | 26439.2 | 69.8 | 90 |
| Minimum-Maximum | 13390.5–124768.9 | 39.4–264.2 | 15–300 |
| PRAM + ISO mixed, S separate[c] | | | |
| Mean ± SEM | 38033.8 ± 5623.0 | 108.0 ± 18.5 | 159.0 ± 13.7 |
| Median | 30685.5 | 84.4 | 122 |
| Minimum-Maximum | 18887.2–164981.3 | 41.4–525.7 | 60–300 |
| PRAM + ISO + S mixed[d] | | | |
| Mean ± SEM | 33135.3 ± 3849.3 | 84.4 ± 8.8 | 227.0 ± 16.5 |
| Median | 29179.5 | 67.2 | 182 |
| Minimum-Maximum | 14928.9–113737.7 | 36.4–236.4 | 120–510 |
| PBC + ISO + S mixed[e] | | | |
| Mean ± SEM | 35557.0 ± 4340.2 | 91.6 ± 13.8 | 195.9 ± 17.2 |
| Median | 28260.0 | 72.2 | 180 |
| Minimum-Maximum | 17292.5–119896.5 | 39.6–405.4 | 15–365 |

[a] Pramlintide, isophane insulin, and soluble insulin in separate syringes.
[b] Pramlintide + soluble insulin in one syringe, with isophane insulin separate.
[c] Pramlintide + isophane insulin in one syringe with soluble insulin separate.
[d] Pramlintide + isophane insulin + soluble insulin in one syringe.
[e] Placebo (matching pramlintide) + isophane insulin + soluble insulin in one syringe.

Median serum free insulin C$_{max}$ and AUC$_{(0-600)}$ values were comparable after pramlintide was administered in combined injections with soluble insulin with and without isophane insulin (PRAM+ISO+S mixed and PRAM+S mixed, ISO separate, respectively) compared to PRAM, ISO, S separate. Median C$_{max}$ and AUC$_{(0-600)}$ values were slightly larger (27% and 19%, respectively) when pramlintide and isophane insulin were mixed (PRAM+ISO mixed, S separate) compared to PRAM, ISO, S separate. There was a delay in median T$_{max}$ (8% and 33%) associated with mixing pramlintide and isophane insulin without and with soluble insulin (PRAM+ISO mixed, S separate; PRAM+ISO+S mixed, respectively) compared to administration in separate injections. However, median T$_{max}$ occurred earlier (32%) for PRAM+S mixed, ISO separate compared to PRAM, ISO, S separate.

The results lead to the following conclusions for serum free insulin. When pramlintide was mixed with isophane insulin in one syringe and soluble insulin was administered by separate injection, insulin had increased bioavailability compared to other treatments. However, this difference in mean profiles may be clinically indistinguishable, particularly when the high variability in the free insulin concentration data is considered. There was an increase in median insulin C$_{max}$ and a slight delay in T$_{max}$ associated with mixing pramlintide with isophane insulin compared to administration in separate injections. Insulin bioavailability appeared to be unaffected when pramlintide was mixed with soluble insulin with and without isophane insulin. There was a decrease in median $T_{max}$ when pramlintide was mixed with soluble insulin without isophane insulin. The free insulin profiles following administration of pramlintide, soluble insulin, and isophane insulin in a single injection were similar to those following administration of placebo, soluble insulin, and isophane insulin in a single injection. Finally, a slight delay in $T_{max}$ was observed following administration of PRAM+ISO+S mixed relative to PBO+ISO+S mixed.

Figure 24:
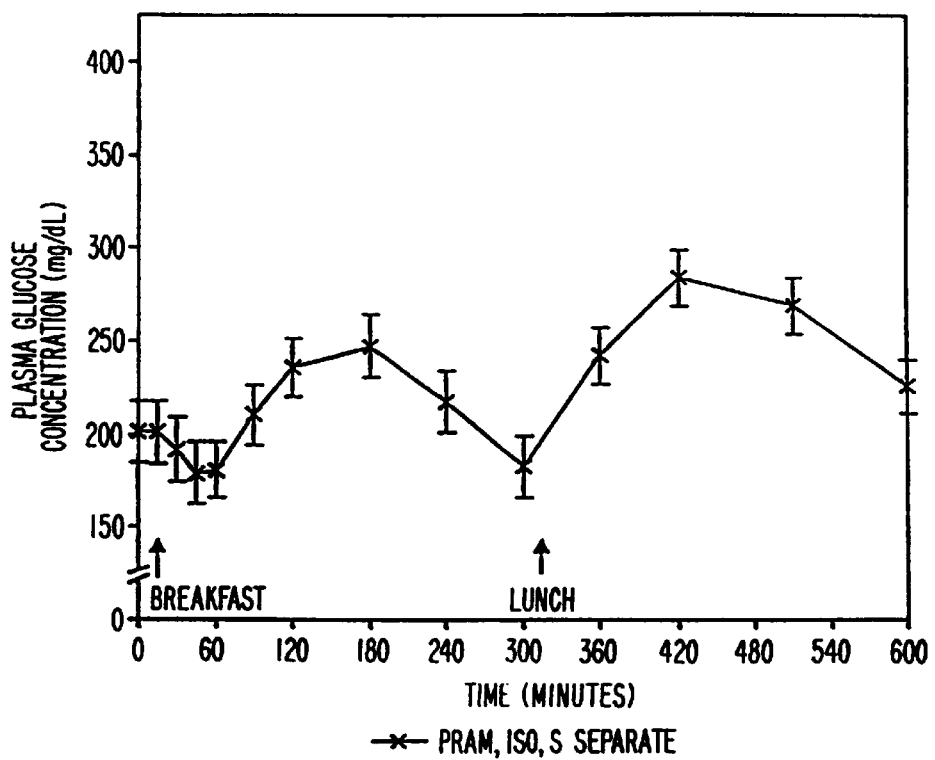
FIG. 24 shows plasma glucose concentrations after subcutaneous administration of pramlintide, isophane insulin, and soluble insulin in separate injections in patients with Type I diabetes mellitus (Mean±SEM; N=28).

Plasma Glucose Concentrations—Mean plasma glucose concentration-time profiles and parameters are described and compared between treatments. Mean plasma glucose concentration-time profiles for all evaluable patients after all treatments are displayed in FIGS. 24–28. Mean plasma glucose concentrations following administration of PRAM, ISO, S separate are displayed in FIG. 24. Mean plasma glucose concentrations after PRAM, ISO, S separate fluctuated between approximately 180 and 285 mg/dL. Mean plasma glucose concentrations declined from 15 minutes (the time breakfast was provided) to 45 minutes after dosing, after which there was an increase from 60 to 180 minutes, followed by another decline to 300 minutes. From 300 to 420 minutes after dosing, with lunch ingested at 315 minutes, mean plasma glucose concentrations increased. Thereafter, mean plasma glucose concentrations decreased to approximately 225 mg/dL at 600 minutes.

Figure 25:
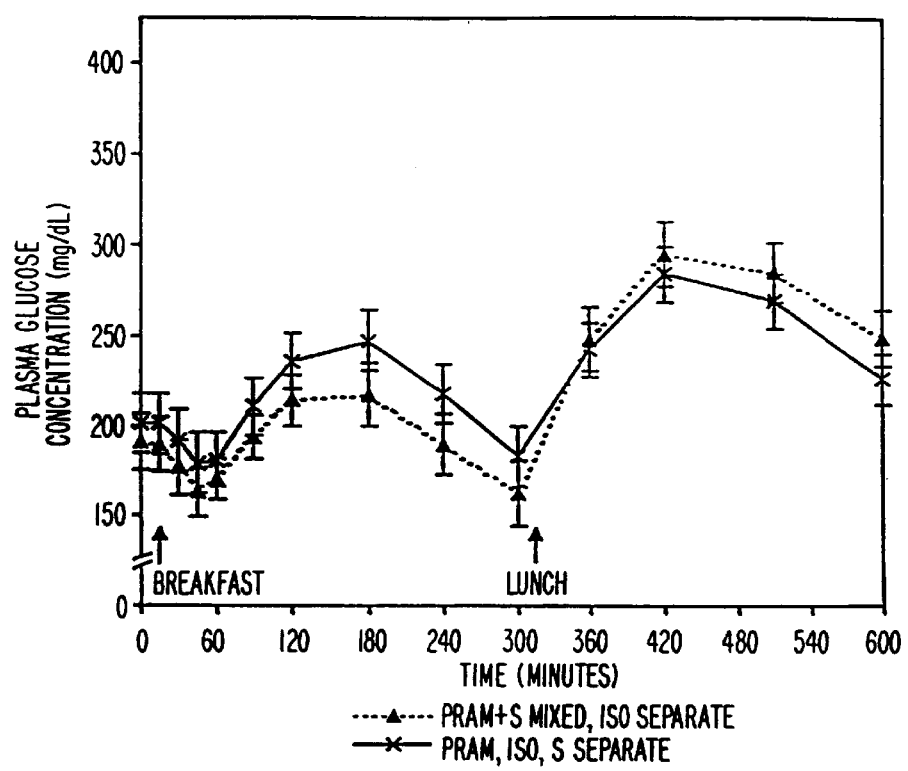
FIG. 25 shows plasma glucose concentrations after subcutaneous administration of pramlintide combined with soluble insulin (PRAM+S mixed, ISO separate) compared to administration of pramlintide, isophane insulin, and soluble insulin in separate injections in patients with Type I diabetes mellitus (Mean±SEM; N=28)

Mean plasma glucose concentrations following PRAM+S mixed, ISO separate compared to PRAM, ISO, S separate are displayed in FIG. 25. Although the shapes of the profiles were similar, mean plasma glucose concentrations following administration of PRAM+S mixed, ISO separate were lower compared to those for PRAM, ISO, S separate from 0 to 300 minutes after dosing. Mean concentrations for PRAM+S mixed, ISO separate fluctuated between approximately 160 and 295 mg/dL. From 360 to 600 minutes after dosing, mean plasma glucose concentrations for PRAM+S mixed, ISO separate were slightly elevated but followed the same time course as the profile for PRAM, ISO, S separate and declined to approximately 250 mg/dL at 600 minutes.

Figure 26:
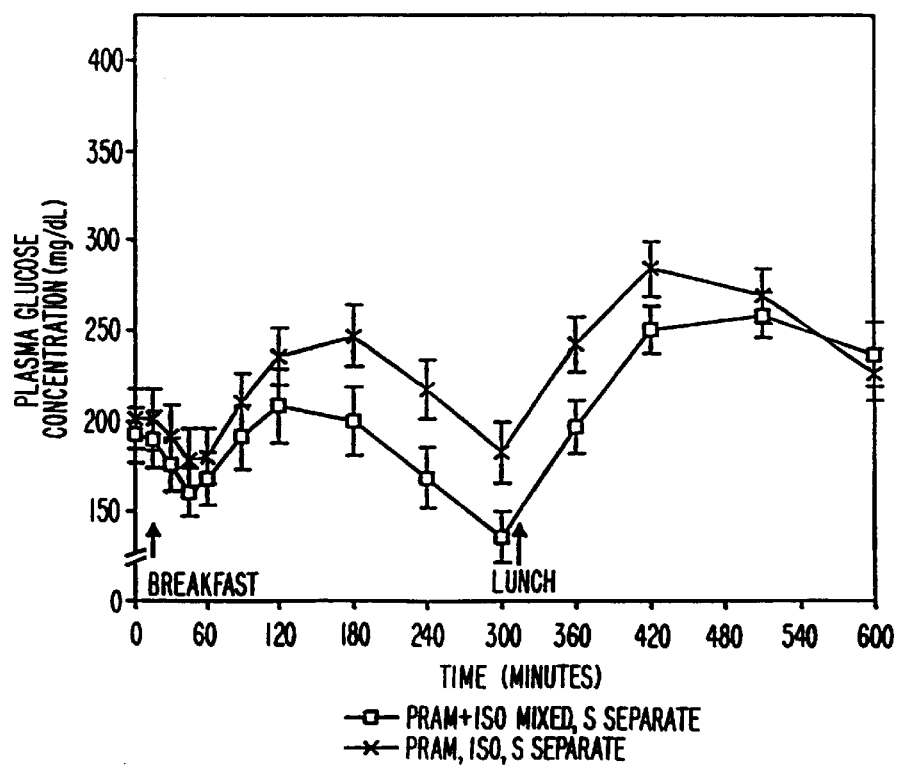
FIG. 26 shows plasma glucose concentrations after subcutaneous administration of pramlintide combined with isophane insulin (PRAM+ISO mixed, S separate) compared to administration of pramlintide, isophane insulin, and soluble insulin in separate injections in patients with Type I diabetes mellitus (Mean±SEM; N=28)

Mean plasma glucose concentrations following administration of PRAM+ISO mixed, S separate compared to PRAM, ISO, S separate are displayed in FIG. 26. Although the shapes of the profiles were similar, mean plasma glucose concentrations following administration of PRAM+ISO mixed, S separate were lower than those for PRAM, ISO, S separate after breakfast and after lunch (from 0 to 510 minutes). Mean concentrations for PRAM+ISO mixed, S separate fluctuated between approximately 135 and 260 mg/dL. At 600 minutes after dosing, the mean plasma glucose concentration had reached approximately 235 mg/dL for PRAM+ISO mixed, S separate, which was similar to that for PRAM, ISO, S separate (225 mg/dL).

Figure 27:
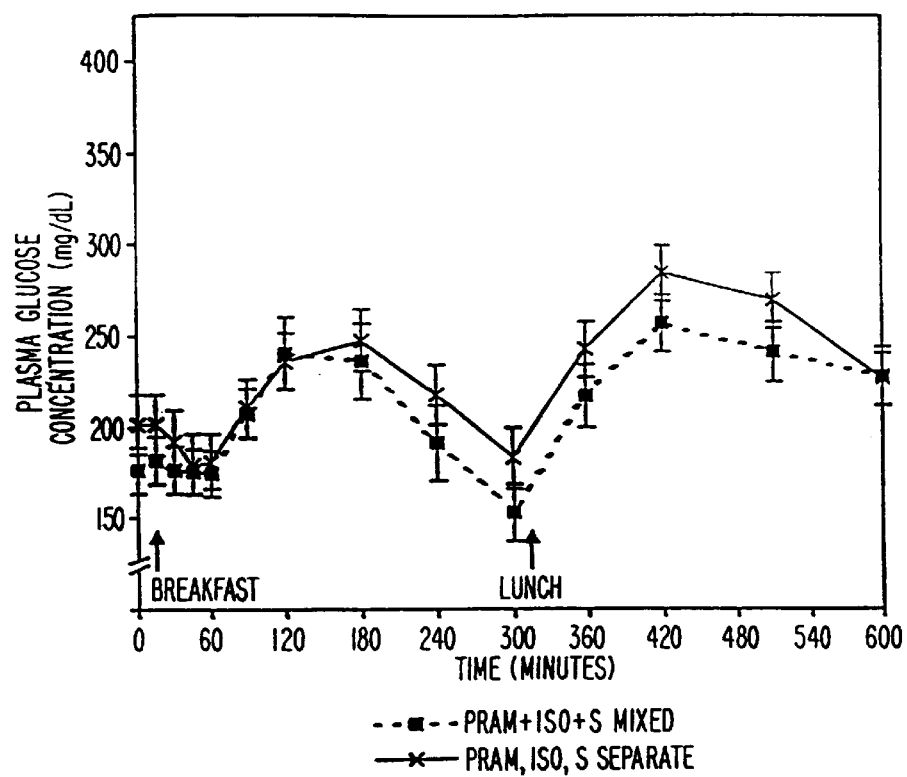
FIG. 27 shows plasma glucose concentrations after subcutaneous administration of pramlintide combined with isophane insulin and soluble insulin (PRAM+ISO+S mixed) compared to administration of pramlintide, isophane insulin, and soluble insulin in separate injections in patients with Type I diabetes mellitus (Mean±SEM; N=28)

Mean plasma glucose concentrations following administration of PRAM+ISO+S mixed compared to PRAM, ISO, S separate are displayed in FIG. 27. The mean plasma glucose concentration profile following administration of PRAM+ISO+S mixed was similar in shape to that after PRAM, ISO, S separate. Mean concentrations for PRAM+ISO+S mixed fluctuated between approximately 150 and 260 mg/dL. The two profiles were almost superimposable between 60 and 120 minutes following administration. From 120 to 600 minutes after dosing, mean plasma glucose concentrations for PRAM+ISO+S mixed were lower but followed the same time course as those after administration of PRAM, ISO, S separate and declined to approximately 225 mg/dL at 600 minutes.

Figure 28:
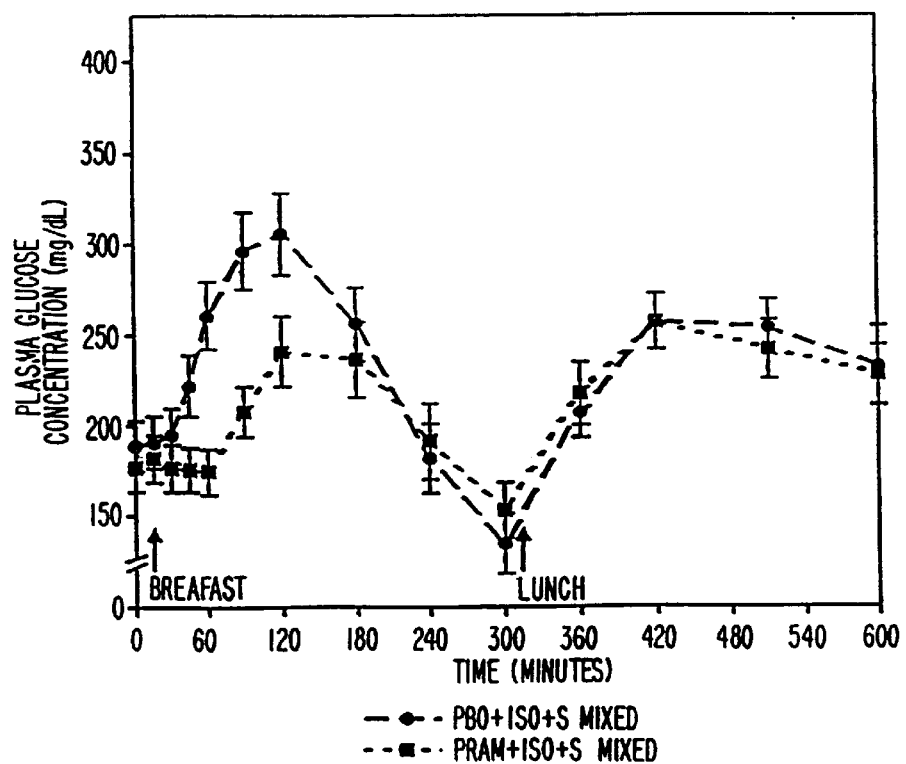
FIG. 28 shows plasma glucose concentrations after subcutaneous administration of pramlintide combined with isophane insulin and soluble insulin (PRAM+ISO+S mixed) compared to administration of placebo combined with isophane insulin and soluble insulin (PBO+ISO+S mixed) in patients with Type I diabetes mellitus (Mean±SEM; N=28).

Mean plasma glucose concentrations following administration of PBO+ISO+S mixed compared to PRAM+ISO+S mixed are displayed in FIG. 28. Mean plasma glucose concentrations were higher after breakfast for up to 180 minutes after administration of PBO+ISO+S mixed compared to PRAM+ISO+S mixed. This is consistent with the effect of pramlintide to lower plasma glucose concentrations following meal ingestion within the first 180 to 240 minutes after dosing. After 300 minutes, the mean plasma glucose concentration profile for PBO+ISO+S mixed was similar to that for PRAM+ISO+S mixed. Mean plasma glucose concentrations were approximately 230 mg/dL at 600 minutes after PBO+ISO+S mixed compared to approximately 225 mg/dL after PRAM+ISO+S mixed.

Plasma glucose $AUC_{(0-600)}$, $C_{max}$, and $T_{max}$ values for all evaluable patients after all treatments are displayed in Table 6.

TABLE 6

Plasma Glucose Pharmacokinetic Parameter Values in Patients with Type I Diabetes Mellitus Following Single Doses of Pramlintide, Soluble Insulin, and Isophane Insulin Administered as Separate and Combined Subcutaneous Injections [Mean + SEM, Median, and Range; N = 28]

| Treatment/ Statistics (mg/dL) | $AUC_{(0-600)}$ (min) | $C_{max}$ (mgCmin/dL) | $T_{max}$ |
|---|---|---|---|
| PRAM, ISO, S separate[a] | | | |
| Mean ± SEM | 141943.0 ± 7685.2 | 326.0 ± 12.8 | 291.6 ± 32.5 |
| Median | 145156.5 | 326.0 | 387.5 |
| Min–Max | 56955–215145 | 175–448 | 0–510 |
| PRAM + S mixed, ISO separate[b] | | | |
| Mean ± SEM | 138742.5 ± 6987.3 | 340.7 ± 12.0 | 356.4 ± 33.7 |
| Median | 132500.0 | 350.5 | 420.0 |
| Min–Max | 57000–234559 | 146–510 | 0–601 |
| PRAM + ISO mixed, S separate[c] | | | |
| Mean ± SEM | 120000.5 ± 6834.5 | 303.3 ± 13.6 | 368.0 ± 37.4 |
| Median | 114735.0 | 311.0 | 420.0 |
| Min–Max | 48683–201939 | 131–465 | 0–600 |
| PRAM + ISO + S mixed[d] | | | |
| Mean ± SEM | 127864.4 ± 7776.3 | 313.1 ± 14.5 | 304.0 ± 37.7 |
| Median | 126720.8 | 313.0 | 272.5 |
| Min–Max | 56005–202065 | 157–461 | 0–600 |
| PBO + ISO + S mixed[e] | | | |
| Mean ± SEM | 137711.1 ± 6983.4 | 369.0 ± 13.5 | 266.1 ± 36.3 |
| Median | 132631.0 | 381.0 | 122.0 |
| Minimum-Maximum | 58515–206558 | 205–481 | 58–600 |

[a]Pramlintide, soluble insulin, and isophane insulin in separate syringes.
[b]Pramlintide + soluble insulin in one syringe, with isophane insulin separate.
[c]Pramlintide + isophane insulin in one syringe, with soluble insulin separate.
[d]Pramlintide + isophane insulin + soluble insulin in one syringe.
[e]Placebo (matching pramlintide) + isophane insulin + soluble insulin in one syringe.

Mean baseline plasma glucose concentrations were approximately 175 to 200 mg/dL for all treatments. Median $AUC_{(0-600)}$ and $C_{max}$ values were comparable when pramlintide was mixed with soluble insulin (PRAM+S mixed, ISO separate) compared to administration in separate injections. The median $AUC_{(0-600)}$ and $C_{max}$ values for PRAM+ISO mixed, S separate and median $AUC_{(0-600)}$ value for PRAM+ISO+S mixed were slightly lower than that for PRAM, ISO, S separate. Although median $T_{max}$ values were comparable when pramlintide was mixed with insulin compared to administration in separate injections, mean $T_{max}$ values were delayed (141% to 181%) for the combined injections compared to separate injections. Significant deviations from normality were not observed for the $\log_e$-transformed values for the variables $C_{max}$ and $AUC_{(0-600)}$ for plasma glucose. There was no period effect observed during statistical analysis of the data.

The analyses for plasma glucose demonstrate several points. First, although median $T_{max}$ values were comparable, mean $T_{max}$ values indicated a delay in $T_{max}$ associated with mixing pramlintide with isophane and/or soluble insulin compared to administration in separate injections. Median $C_{max}$ was comparable between the pramlintide combined and separate treatments. Administration of pramlintide combined with isophane insulin resulted in a slightly lower glucose profile ($AUC_{(0-600)}$) while pramlintide and soluble insulin in a combined injection resulted in a comparable glucose profile to that following administration of pramlintide, isophane insulin, and soluble insulin in separate injections. Median glucose $C_{max}$ values were lower (18%), between-treatment comparisons for glucose $C_{max}$ were statistically significant (p=0.0010), and $T_{max}$ values were not significantly different after administration of pramlintide, soluble insulin, and isophane insulin combined in a single injection relative to placebo, soluble insulin, and isophane insulin combined in a single injection. Between 45 and 180 minutes after dosing, administration of the four pramlintide treatments resulted in lower overall glucose profiles compared to that after administration of the placebo treatment. By 300 minutes after dosing, the mean plasma glucose concentrations for the pramlintide and placebo treatments were similar. After 300 minutes, the glucose profiles were similar for the placebo treatment and for pramlintide mixed with isophane insulin with and without soluble insulin.

Thus, it is concluded for plasma glucose that over the entire time period (0 to 600 minutes), the glucose profile was clinically optimal with the combination of pramlintide and isophane insulin in one syringe with or without soluble insulin compared to the other treatments.

With regard to plasma glucose during the breakfast period, it is concluded that median glucose $C_{max}$ and $T_{max}$ values were comparable associated with mixing pramlintide with soluble and/or isophane insulin compared to administration in separate injections. There was a slight decrease in median glucose $AUC_{(0-300)}$ values for the treatments in which pramlintide was mixed with soluble and/or isophane insulin relative to administration in separate injections. Median glucose $C_{max}$ values were lower (14%) and median glucose $T_{max}$ values were comparable after administration of pramlintide, soluble insulin, and isophane insulin combined in a single injection relative to placebo, soluble insulin, and isophane insulin combined in a single injection. Between-treatment comparisons for glucose $C_{max}$ were significant (p=0.0481). Administration of pramlintide mixed with soluble and isophane insulin resulted in a lower glucose profile compared to that after administration of the placebo treatment.

With regard to plasma glucose during the lunch period it is concluded that median plasma glucose profiles were lower after lunch following administration of pramlintide mixed with isophane insulin with and without soluble insulin compared to administration in separate injections. Median glucose $C_{max}$ and $T_{max}$ values were comparable when pramlintide was combined with insulin prior to injection relative to administration in separate injections. Following administration of pramlintide, soluble, and isophane insulin in a combined injection, the median glucose $C_{max}$ value was lower compared to that for the placebo combined injection.

The study demonstrates overall that there is an advantage, with respect to the magnitude and duration of glucose control, to mixing pramlintide and isophane insulin prior to injection, and that there is no disadvantage to mixing pramlintide with soluble insulin and/or isophane insulin prior to injection.

EXAMPLE 3

Preparation of $^{25,28,29}$Pro-h-Amylin

Solid phase synthesis of $^{25,28,29}$Pro-h-amylin using methylbenzhydryl-amine anchor-bond resin and $N^\alpha$-Boc/benzyl-side chain protection was carried out by standard peptide synthesis methods. The $^{2,7}$-[disulfide] fully protected amylin agonist-MBHA-resin was obtained by treatment of Acm-protected cysteines with thallium (III) trifluoroacetate in trifluoroacetic acid. After cyclization was achieved the resin and side chain protecting groups were cleaved with liquid HF in the presence of dimethylsulfide and anisole as described above. The $^{25,28,29}$Pro-h-amylin was purified by preparative reversed-phase HPLC. The peptide was found to be homogeneous by analytical HPLC and capillary electrophoresis and the structure confirmed by amino acid analysis and sequence analysis. The product gave the desired mass ion. FAB mass spec: $(M+H)^+=3,949$.

EXAMPLE 4

Preparation of $^{18}$Arp$^{25,28,29}$pro-h-Amylin

Solid phase synthesis of $^{18}$Arg$^{25,28,29}$Pro-h-amylin using methylbenz-hydrylamine anchor-bond resin and $N^\alpha$-Boc/benzyl-side chain protection was carried out by standard peptide synthesis methods. The $^{2,7}$-[disulfide]fully protected amylin agonist-MBHA-resin was obtained by treatment of Acm-protected cysteines with thallium (III) trifluoroacetate in trifluoroacetic acid. After cyclization was achieved the resin and side chain protecting groups were cleaved with liquid HF in the presence of dimethylsulfide and anisole as described above. The $^{18}$Arg$^{25,28,29}$Pro-h-amylin was purified by preparative reversed-phase HPLC. The peptide was found to be homogeneous by analytical HPLC and capillary electrophoresis and the structure confirmed by amino acid analysis and sequence analysis. The product gave the desired mass ion. FAB mass spec: $(M+H)^+=3,971$.

EXAMPLE 5

Preparation of $^{18}$Arg$^{25,28}$Pro-h-Amylin

Solid phase synthesis of $^{18}$Arg$^{25,28}$Pro-h-amylin using methylbenzhydrylamine anchor-bond resin and $N^\alpha$-Boc/benzyl-side chain protection was carried out by standard peptide synthesis methods. The $^{2,7}$-[disulfide]fully protected amylin agonist-MBHA-resin was obtained by treatment of Acm-protected cysteines with thallium (III) trifluoroacetate in trifluoroacetic acid. After cyclization was achieved the resin and side chain protecting groups were cleaved with liquid HF in the presence of dimethylsulfide and anisole as described above. The $^{18}$Arg$^{25,28}$Pro-h-amylin was purified by preparative reversed-phase HPLC. The peptide was found to be homogeneous by analytical HPLC and capillary electrophoresis and the structure confirmed by amino acid analysis and sequence analysis. The product gave the desired mass ion. FAB mass spec: $(M+H)^+=3,959$.

EXAMPLE 6

Receptor Binding Assay

Evaluation of the binding of compounds to amylin receptors was carried out as follows. $^{125}$I-rat amylin (Bolton- Hunter labeled at the N-terminal lysine) was purchased from Amersham Corporation (Arlington Heights, Ill.). Specific activities at time of use ranged from 1950 to 2000 Ci/mmol. Unlabeled peptides were obtained from BACHEM Inc. (Torrance, Calif.) and Peninsula Laboratories (Belmont, Calif.).

Male Sprague-Dawley rats (200–250) grams were sacrificed by decapitation. Brains were removed to cold phosphate-buffered saline (PBS). From the ventral surface, cuts were made rostral to the hypothalamus, bounded laterally by the olfactory tracts and extending at a 45E angle medially from these tracts. This basal forebrain tissue, containing the nucleus accumbens and surrounding regions, was weighed and homogenized in ice-cold 20 mM HEPES buffer (20 mM HEPES acid, pH adjusted to 7.4 with NaOH at 23EC). Membranes were washed three times in fresh buffer by centrifugation for 15 minutes at 48,000×g. The final membrane pellet was resuspended in 20 mM HEPES buffer containing 0.2 mM phenylmethylsulfonyl fluoride (PMSF).

To measure $^{125}$1-amylin binding, membranes from 4 mg original wet weight of tissue were incubated with $^{125}$I-amylin at 12–16 pM in 20 mM HEPES buffer containing 0.5 mg/ml bacitracin, 0.5 mg/ml bovine serum albumin, and 0.2 mM PMSF. Solutions were incubated for 60 minutes at 23EC. Incubations were terminated by filtration through GF/B glass fiber filters (Whatman Inc., Clifton, N.J.) which had been presoaked for 4 hours in 0.3% poylethyleneimine in order to reduce nonspecific binding of radiolabeled peptides. Filters were washed immediately before filtration with 5 ml cold PBS, and immediately after filtration with 15 ml cold PBS. Filters were removed and radioactivity assessed in a gamma-counter at a counting efficiency of 77%. Competition curves were generated by measuring binding in the presence of $10^{-12}$ to $10^{-6}$ M unlabeled test compound and were analyzed by nonlinear regression using a 4-parameter logistic equation (Inplot program; GraphPAD Software, San Diego).

In this assay, purified human amylin binds to its receptor at a measured $IC_{50}$ of about 50 pM. Results for test compounds are set forth in Table I, showing that each of the compounds has significant receptor binding activity.

EXAMPLE 7

Soleus Muscle Assay

Determination of amylin agonist activity of compounds was carried out using the soleus muscle assay as follows. Male Harlan Sprague-Dawley rats of approximately 200 g mass were used in order to maintain mass of the split soleus muscle less than 40 mg. The animals were fasted for 4 hours prior to sacrifice by decapitation. The skin was stripped from the lower limb which was then pinned out on corkboard. The tendo achilles was cut just above os calcis and m. gastrocnemius reflected out from the posterior aspect of the tibia. M. soleus, a small 15–20 mm long, 0.5 mm thick flat muscle on the bone surface of m. gastrocnemius was then stripped clear and the perimysium cleaned off using fine scissors and forceps. M. soleus was then split into equal parts using a blade passed antero-posteriorly through the belly of the muscle to obtain a total of 4 muscle strips from each animal. After dissecting the muscle from the animal, it was kept for a short period in physiological saline. It was not necessary that the muscle be held under tension as this had no demonstrable effects on radioglucose incorporation into glycogen.

Muscles were added to 50 mL Erlenmeyer flasks containing 10 mL of a pregassed Krebs-Ringer bicarbonate buffer containing (each liter) NaCl 118.5 mmol (6.93 g), KCl 5.94 mmol (443 mg), $CaCl_2$ 2.54 mmol (282 mg), $MgSO_4$ 1.19 mmol (143 mg), $KH_2PO_4$ 1.19 mmol (162 mg), $NaHCO_3$ 25 mmol (2.1 g), 5.5 mmol glucose (1 g) and recombinant human insulin (Humulin-R, Eli Lilly, Ind.) and the test compound, as detailed below. pH at 37EC was verified as being between 7.1 and 7.4. Muscles were assigned to different flasks so that the 4 muscle pieces from each animal were evenly distributed among the different assay conditions. The incubation media were gassed by gently blowing carbogen (95% $O_2$, 5% $CO_2$) over the surface while being continuously agitated at 37EC in an oscillating water bath. After a half-hour "preincubation" period, 0.5: Ci of U-$^{14}$C-glucose was added to each flask which was incubated for a further 60 minutes. Each muscle piece was then rapidly removed, blotted and frozen in liquid $N_2$, weighed and stored for subsequent determination of $^{14}$C-glycogen.

$^{14}$C-glycogen determination was performed in a 7 mL scintillation vial. Each frozen muscle specimen was placed in a vial and digested in 1 mL 60% potassium hydroxide at 70 EC for 45 minutes under continuous agitation. Dissolved glycogen was precipitated out onto the vial by the addition of 3 mL absolute ethanol and overnight cooling at $-20$ EC. The supernatant was gently aspirated, the glycogen washed again with ethanol, aspirated and the precipitate dried under vacuum. All ethanol is evaporated to avoid quenching during scintillation counting. The remaining glycogen was redissolved in 1 mL water and 4 mL scintillation fluid and counted for $^{14}$C.

The rate of glucose incorporation into glycogen (expressed in :mol/g/hr) was obtained from the specific activity of $^{14}$C-glucose in the 5.5 mM glucose of the incubation medium, and the total $^{14}$C counts remaining in the glycogen extracted from each muscle. Dose/response curves were fitted to a 4-parameter logistic model using a least-squares iterative routine (ALLFIT, v2.7, NIH, Md.) to derive $EC_{50}$'s. Since $EC_{50}$ is log-normally distributed, it is expressed +standard error of the logarithm. Pairwise comparisons were performed using t-test based routines of SYSTAT (Wilkinson, "SYSTAT: the system for statistics," SYSTAT Inc., Evanston Ill. (1989)).

Dose response curves were generated with muscles added to media containing 7.1 nM (1000:U/mL) insulin and each test compound added at final (nominal) concentrations of 0, 1, 3, 10, 30, 100, 300 and 1000 nM. Each assay also contained internal positive controls consisting of a single batch of archived rat amylin, lyophilized and stored at $-70$ EC.

Human amylin is a known hyperglycemic peptide, and $EC_{50}$ measurements of amylin preparations in the soleus muscle assay range typically from about 1–10 nM, although some commercial preparations which are less than 90% pure have higher $EC_{50}$'s due to the presence of contaminants that result in a lower measured activity. Results for test compounds are set forth in Table A.

TABLE A

| | Receptor Binding Assay $IC_{50}$(pM) | Soleus Muscle Assay $EC_{50}$(nM) |
|---|---|---|
| 1) $^{25}$Pro$^{26}$Val$^{28,29}$Pro-h-Amylin | 18.0 | 4.68 |
| 2) $^{2,7}$Cyclo-[$^2$Asp,$^7$Lys]-h-Amylin | 310.0 | 6.62 |
| 3) $^{2-37}$h-Amylin | 236.0 | 1.63 |
| 4) $^1$Ala-h-Amylin | 148.0 | 12.78 |
| 5) $^1$Ser-h-Amylin | 33.0 | 8.70 |
| 6) $^{25,28}$Pro-h-Amylin | 26.0 | 13.20 |
| 7) des-$^1$Lys$^{25,28}$Pro-h-Amylin | 85.0 | 7.70 |
| 8) $^{18}$Arg$^{25,28}$Pro-h-Amylin | 32.0 | 2.83 |

TABLE A-continued

|   | Receptor Binding Assay $IC_{50}(pM)$ | Soleus Muscle Assay $EC_{50}(nM)$ |
|---|---|---|
| 9) des-$^1$Lys$^{18}$Arg$^{25,28}$Pro-h-Amylin | 82.0 | 3.77 |
| 10) $^{18}$Arg$^{25,28,29}$Pro-h-Amylin | 21.0 | 1.25 |
| 11) des-$^1$Lys$^{18}$Arg$^{25,28,29}$Pro-h-Amylin | 21.0 | 1.86 |
| 12) $^{25,28,29}$Pro-h-Amylin | 10.0 | 3.71 |
| 13) des-$^1$Lys$^{25,28,29}$Pro-h-Amylin | 14.0 | 4.15 |

EXAMPLE 8

PHENOL RED GASTRIC EMPTYING ASSAY

Gastric emptying was measured using a modification (Plourde et al., Life Sci. 53:857–862 (1993)) of the original method of Scarpignato et al. (Arch. Int. Pharmacodyn. Ther. 246:286–295 (1980)). Briefly, conscious rats received by gavage. 1.5 mL of an acoloric gel containing 1.5% methyl cellulose (M-0262, Sigma Chemical Co., St. Louis, Mo.) and 0.05% phenol red indicator. Twenty minutes after gavage, rats were anesthetized using 5% halothane, the stomach exposed and clamped at the pyloric and lower esophageal sphincters using artery forceps, removed and opened into an alkaline solution which was made up to a fixed volume. Stomach content was derived from the intensity of the phenol red in the alkaline solution, measured by absorbance at a wavelength of 560 nm. In most experiments, the stomach was clear. In other experiments, particulate gastric contents were centrifuged to clear the solution for absorbance measurements. Where the diluted gastric contents remained turbid, the spectroscopic absorbance due to phenol red was derived as the difference between that present in alkaline vs acetified diluent. In separate experiments on 7 rats, the stomach and small intestine were both excised and opened into an alkaline solution. The quantity of phenol red that could be recovered from the upper gastrointestinal tract within 29 minutes of gavage was 89±4%; dye which appeared to bind irrecoverably to the gut luminal surface may have accounted for the balance. To compensate for this small loss, percent of stomach contents remaining after 20 minutes were expressed as a fraction of the gastric contents recovered from control rats sacrificed immediately after gavage in the same experiment. Percent gastric emptying contents remaining=(absorbance at 20 min)/(absorbance at 0 min) Dose response curves for gastric emptying were fitted to a 4-parameter logistic model using a least-squares iterative routine (ALLFIT, v2.7, NIH, Bethesda, Md.) to derive $ED_{50}$s. Since $ED_{50}$ is log-normally distributed, it is expressed±standard error of the logarithm. Pairwise comparisons were performed using one-way analysis of variance and the Student-Newman-Keuls multiple comparisons test (Instat v2.0, GraphPad Software, San Diego, Calif.) using P<0.05 as the level of significance.

In dose response studies, rat amylin (Bachem, Torrance, Calif.) dissolved in 0.15M saline, was administered as a 0.1 mL subcutaneous bolus in doses of 0, 0.01, 0.1, 1, 10 or 100 Fg 5 minutes before gavage in Harlan Sprague Dawley (non-diabetic) rats fasted 20 hours and diabetic BB rats fasted 6 hours. When subcutaneous amylin injections were given 5 minutes before gavage with phenol red indicator, there was a dose-dependent suppression of gastric emptying (data not shown). Suppression of gastric emptying was complete in normal HSD rats administered 1 Fg of amylin, and in diabetic rats administered 10 Fg (P=0.22, 0.14). The $ED_{50}$ for inhibition of gastric emptying in normal rats was 0.43 Fg (0.60 nmol/kg)±0.19 log units, and was 2.2 Fg (2.3 nmol/kg)±0.18 log units in diabetic rats.

EXAMPLE 9

TRITIATED GLUCOSE GASTRIC EMPTYING ASSAY

Conscious, non-fasted, Harlan Sprague Dawley rats were restrained by the tail, the tip of which was anesthetized using 2% lidocaine. Tritium in plasma separated from tail blood collected 0, 15, 30, 60, 90 and 120 minutes after gavage was detected in a beta counter. Rats were injected subcutaneously with 0.1 mL saline containing 0, 0.1, 0.3, 1, 10 or 100 Fg of rat amylin 1 minute before gavage (n=8,7,5,5,5, respectively). After gavage of saline pre-injected rats with tritiated glucose, plasma tritium increased rapidly (t ½ of about 8 minutes) to an asymptote that slowly declined. Subcutaneous injection with amylin dose-dependently slowed and/or delayed the absorption of the label. Plasma tritium activity was integrated over 30 minutes to obtain the areas under the curve plotted as a function of amylin dose. The $ED_{50}$ derived from the logistic fit was 0.35 Fg of amylin.

We claim:

1. A pharmaceutical composition comprising effective glucose-lowering amounts of an amylin agonist peptide and an intermediate-acting insulin.

2. The pharmaceutical composition of claim 1 wherein said intermediate-acting insulin is an NPH insulin.

3. The pharmaceutical composition of either of claims 1 or 2 wherein said amylin agonist peptide is pramlintide.

4. The pharmaceutical composition of either of claims 1 or 2 wherein said amylin agonist peptide is an amylin.

5. A method of treating a subject with diabetes which comprises mixing together effective glucose-lowering amounts of an amylin agonist peptide and an intermediate-acting insulin and administering said mixture to said subject.

6. The method of claim 5 wherein said intermediate-acting insulin is an NPH insulin.

7. The method of either of claims 5 or 6 wherein said amylin agonist peptide is pramlintide.

8. The method of either of claims 5 or 6 wherein said amylin agonist peptide is an amylin.

* * * * *